United States Patent
Ono

(10) Patent No.: US 8,728,506 B2
(45) Date of Patent: May 20, 2014

(54) DURABLE PEST REPELLENT AND PEST REPELLENT RESIN COMPOSITION

(75) Inventor: Yasuharu Ono, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 6 days.

(21) Appl. No.: 13/499,234

(22) PCT Filed: Sep. 16, 2010

(86) PCT No.: PCT/JP2010/066043
§ 371 (c)(1),
(2), (4) Date: May 7, 2012

(87) PCT Pub. No.: WO2011/040252
PCT Pub. Date: Apr. 7, 2011

(65) Prior Publication Data
US 2012/0213836 A1    Aug. 23, 2012

(30) Foreign Application Priority Data

Sep. 30, 2009 (JP) ................... 2009-225830
Sep. 30, 2009 (JP) ................... 2009-225831

(51) Int. Cl.
*A01N 25/00* (2006.01)
*A01N 43/40* (2006.01)
*A61K 31/445* (2006.01)
*A61K 31/165* (2006.01)
*A01N 37/18* (2006.01)

(52) U.S. Cl.
USPC ............... 424/405; 514/315; 514/617

(58) Field of Classification Search
CPC ... A01N 2300/00; A01N 25/34; A01N 25/10; A01N 63/00
USPC ................... 424/405; 514/315, 617
See application file for complete search history.

(56) References Cited

U.S. PATENT DOCUMENTS

2003/0161866 A1* 8/2003 Kostyniak et al. ............ 424/449

FOREIGN PATENT DOCUMENTS

| JP | 59-199602 A | 11/1984 |
|---|---|---|
| JP | 3-161402 A | 7/1991 |
| JP | 9-31245 A | 2/1997 |
| JP | 2000-281504 A | 10/2000 |
| JP | 2000-302613 A | 10/2000 |
| JP | 2007-291097 A | 11/2007 |
| JP | 2009-242279 A | 10/2009 |

OTHER PUBLICATIONS

Ichimura (JP 2007-063185 machine translated).*
International Search Report issued in PCT/JP2010/066043 dated Oct. 26, 2010.

* cited by examiner

*Primary Examiner* — Blessing M Fubara
(74) *Attorney, Agent, or Firm* — Birch, Stewart, Kolasch & Birch, LLP

(57) ABSTRACT

Disclosed is a pest repellent that has excellent heat resistance and solvent resistance, that can be kneaded into a resin molded article or a synthetic fiber, and that has excellent durability and persistence for which a pest repellent effect is sustained for a long period even when it is used for a long period or washed. A durable pest repellent that has both high heat resistance and persistence has been accomplished by supporting on a specific layered silicate a pest repellent chemical containing as an essential component at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester.

8 Claims, 8 Drawing Sheets

DURABLE PEST REPELLENT AND PEST REPELLENT RESIN COMPOSITION

TECHNICAL FIELD

The present invention relates to a pest repellent and a pest repellent resin composition that have excellent heat resistance and solvent resistance and can sustain the effect for a long time. More specifically, it is a durable pest repellent having heat resistance and solvent resistance that can be kneaded into a resin molded article or a synthetic fiber, and the pest repellent resin composition so obtained has excellent durability such that the pest repellent effect is sustained even when used for a long period or washed.

BACKGROUND ART

Conventionally, most chemicals known as pest repellents are volatile or sublime, and when they are applied to processed products such as fiber products, resin molded articles, electronic equipment, and print inks, they instantaneously dissipate due to heat, solvent, etc. during processing, the effect is lost, and the human body and the environment are badly affected.

As measures for such problems, JP-A-3-161402 (JP-A denotes a Japanese unexamined patent application publication) discloses a cockroach repellent in which release of a chemical is suppressed by covering with a metal foil one side of a plate formed by kneading a pyrethroid-based insect repellent into a synthetic resin; however, due to the shape being restricted the application thereof is also limited, and since resistance to heat or solvent during molding or processing is not improved, there is the unsolved problem that even when one side of the plate is covered, the chemical is easily released and lost from the opposite side.

Furthermore, JP-A-2000-302613 discloses a repellent in which a pyrethroid-based compound is supported on a layered phosphate or a layered silicate, thus imparting heat resistance and persistence. Although a pyrethroid-based compound has an insecticidal effect, its repellent effect is weak at room temperature, resistant insects emerge, there is a problem with safety, etc., and the range of applications is limited.

JP-A-09-031245 proposes a slow-acting function-imparting agent in which an organic function-imparting agent is supported on a water-absorbing inorganic substance having the ability to bind water of crystallization, and there is an example in which persistence with an effect after 500 hours in a weather resistance test is exhibited by subjecting a synthetic hydrotalcite or a Y-type zeolite to an exhaustive treatment with N,N-diethyl-m-toluamide and carrying out kneading into a polypropylene resin at 250° C. However, since N,N-diethyl-m-toluamide cannot easily be immobilized between layers of a synthetic hydrotalcite or within pores of a Y-type zeolite, this exhaustive treatment does not give sufficient durability to a chemical, and it is an imperfect treatment that gives no more than a simple mixture of a chemical and an inorganic support.

A complex formed by utilizing simple physical adsorption onto a substrate surface might exhibit some degree of gradual release due to the adsorptive power, but since physical adsorption is not accompanied by a large energy such as a change in the crystal structure or chemical bonding, it cannot exhibit a large change in heat resistant temperature or marked durability. In reality, it cannot be said that this exhaustive treatment gives sufficient durability, and there are problems such as foaming being caused if the molding temperature or molding retention time is increased, and bleed-out being caused if a molded article is stored indoors for a long period.

Furthermore, Pharmaceutical and Food Safety Bureau Notification No. 0824003 issued by the Ministry of Health, Labour, and Welfare on 24 Aug. 2005 states that attention should be given to the safety of N,N-diethyl-m-toluamide, and there is a need for a pest repellent having not only high durability but also high safety.

As an example involving something other than simple physical adsorption onto a solid surface, JP-A-2007-291097 proposes a clay mineral-based complex material in which a clay mineral having cation exchangeability between layers is used as a main starting material, and with regard to a combination of an alkali or alkaline earth metal and a bioactive organic compound, which replaces interlayer water between the layers, the organic compound is incorporated between the layers in a stable or semi-stable state. Specifically, a clay mineral-based complex material is cited as an example that can maintain insect repellency for a long period by incorporating N,N-diethyl-m-toluamide, which is a pest repellent, between layers of montmorillonite, which is a clay mineral.

In this treatment, a powder X-ray diffraction analysis of the complex confirmed that the organic chemical is present between the layers of the clay mineral, and although the stability at room temperature is excellent, it cannot be said that it has excellent heat resistance and sufficient durability. Furthermore, since a natural clay mineral is used as a starting material, there is the problem of a resin being colored. That is, although including an organic chemical between layers of an inorganic compound having a layered structure was attempted, due to the selection of the inorganic compound and the organic chemical being poor, the durability of the complex was insufficient, and there was a problem with coloration.

RELATED ART DOCUMENTS

Patent Documents

Patent Document 1: JP-A-3-161402
Patent Document 2: JP-A-2000-302613
Patent Document 3: JP-A-9-031245
Patent Document 4: JP-A-2007-291097

SUMMARY OF THE INVENTION

Problems to be Solved by the Invention

It is an object of the present invention to provide a durable pest repellent that has excellent heat resistance and solvent resistance and can be kneaded into a resin molded article or a synthetic fiber, and a pest repellent resin composition having excellent durability and persistence such that a pest repellent effect lasts for a long period even when used for a long period or washed.

Means for Solving the Problems

In order to solve the above-mentioned problems, in the present invention, a pest repellent chemical containing as an essential component at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester is supported on a specific layered silicate, thus completing a durable pest repellent having both high heat resistance and persistence and a pest repellent resin composition comprising the durable pest repellent and a resin.

MODES FOR CARRYING OUT THE INVENTION

Figure 1:
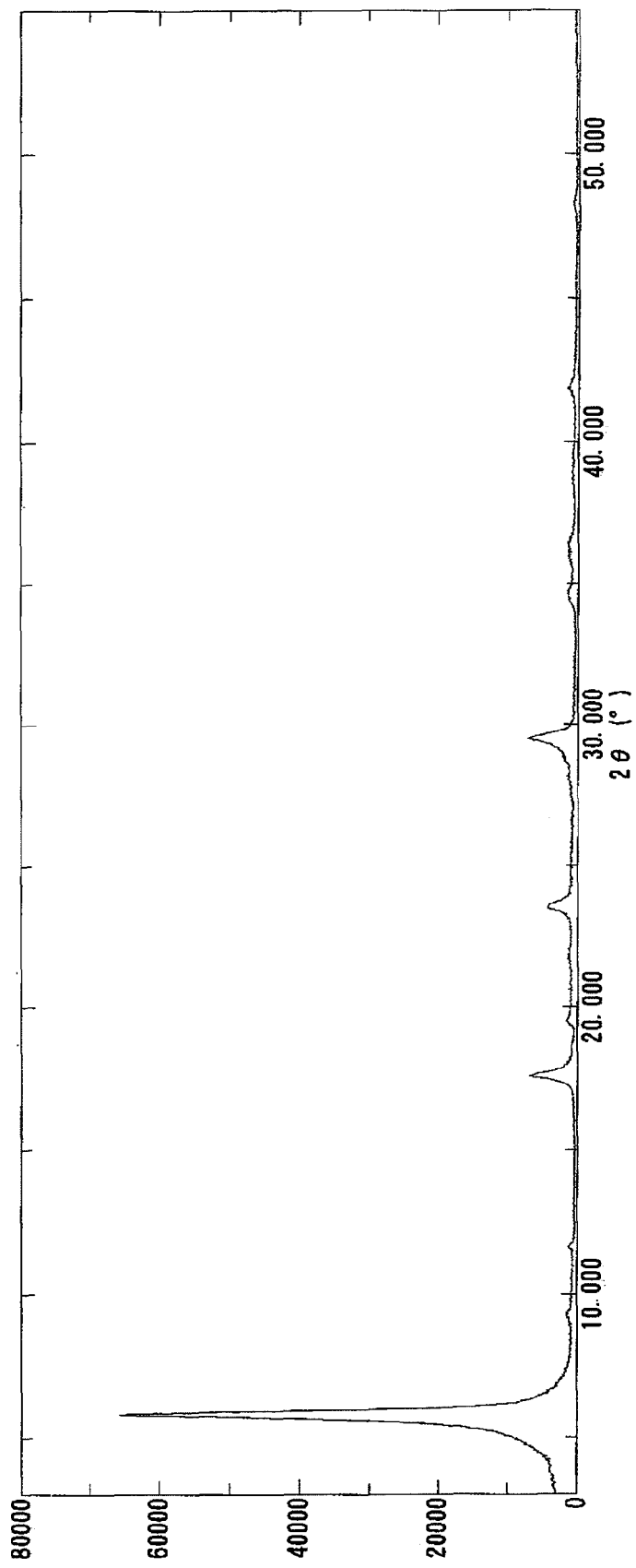
FIG. 1: Powder X-ray diffraction pattern of durable pest repellent 1-4 obtained in Example 1-4.
Figure 2:
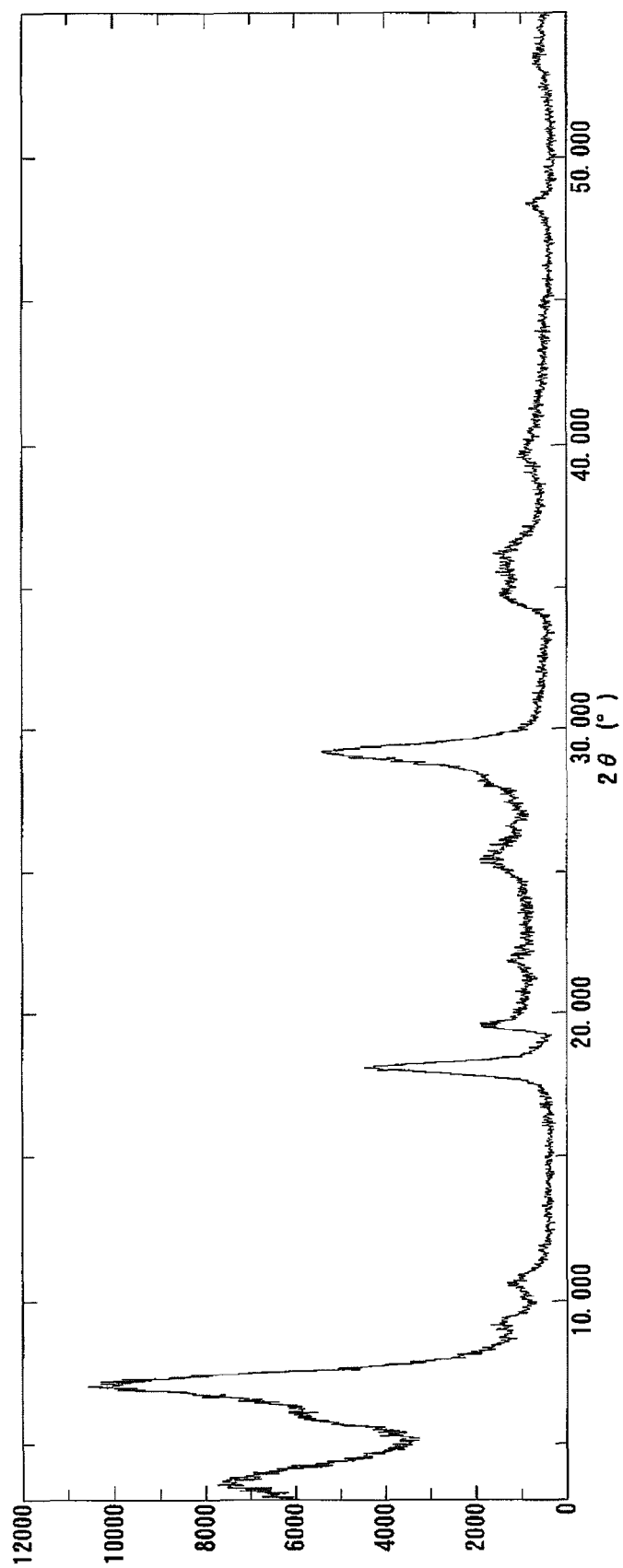
FIG. 2: A powder X-ray diffraction pattern of comparative pest repellent 1-1 obtained in Comparative Example 1-1.

A mode for carrying out the present invention is explained in detail below.

The durable pest repellent of the present invention is one in which a pest repellent chemical containing as an essential component at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester is supported within layers of a layered silicate represented by Formula [1] below.

$$(M^1)_a[Mg_b,(M^2)_c](Si_4O_{10})(A)_2 \quad [1]$$

Here, ($M^1$) is Ca and/or Zn, ($M^2$) is Li and/or Na, and (A) means F and/or OH.

Furthermore, $2a+2b+c=6$, and $0.001 < c \le 0.55$.

<Pest Repellent Chemical>

The pest repellent chemical used in the present invention contains as an essential component at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester, which have a high pest repellent effect and high safety. N,N-Diethyl-m-toluamide, also abbreviated to DEET, is a pest repellent chemical, and may contain a substitution isomer such as a p-toluamide or one in which the N-ethyl group moiety is replaced by another alkyl group having 1 to 3 carbons. N,N-Diethyl-m-toluamide is a liquid at normal temperature and has safety such that it can be sprayed directly onto the skin as it is. With regard to the efficacy, it has excellent pest repellency toward mosquito, black fly, mite, lice, stable fly, bed bug, flea, trombiculid mite, land leech, etc. However, N,N-diethyl-m-toluamide has the property of dissolving a resin as a solvent, and has the defect that if it adheres to skin, clothing, etc. and then contacts a resin machine component, a resin button or fastener, etc. the surface is dissolved to thus degrade the appearance or strength, and is also known to have the defect of having poor heat resistance or water resistance as it is.

1-Piperidinecarboxylic acid-2-(2-hydroxyethyl)-1-methylpropyl ester is a pest repellent chemical that is also known under the name of Picaridin, Icaridin, etc., and has a high pest repellent effect and high safety. 1-Piperidinecarboxylic acid-2-(2-hydroxyethyl)-1-methylpropyl ester is a liquid substance at normal temperature with a boiling point of 272° C. and a flash point of 142° C. In Europe and America, it is an insecticide usually used as an insect repellent spray and has safety such that it can be sprayed directly onto the skin. With regard to the efficacy, it has excellent pest repellency toward mosquito, black fly, mite, lice, stable fly, bed bug, flea, trombiculid mite, land leech, etc.

When either one of N,N-diethyl-m-toluamide or 1-piperidinecarboxylic acid-2-(2-hydroxyethyl)-1-methylpropyl ester is used as a pest repellent chemical, the use of N,N-diethyl-m-toluamide is preferable since it has excellent water resistance.

On the other hand, 1-piperidinecarboxylic acid-2-(2-hydroxyethyl)-1-methylpropyl ester is preferable in terms of high safety and the heat resistance of the durable pest repellent in the present invention being higher than the use of N,N-diethyl-m-toluamide on its own. There is no problem in the use in combination of durable pest repellents containing either one of these pest repellent chemicals, and the performance thereof is the sum of the performances of both durable pest repellents.

Furthermore, when a durable pest repellent is produced by using in combination and mixing N,N-diethyl-m-toluamide and 1-piperidinecarboxylic acid-2-(2-hydroxyethyl)-1-methylpropyl ester as pest repellent chemicals, the initial performance of the durable pest repellent thus obtained is the average of the two durable pest repellent chemicals, but performance after a water resistance test or a heat resistance test is better compared with a case in which separate durable pest repellents are used in combination, and when a production process in which two pest repellent chemicals are mixed and supported on a layered silicate is employed, an effect in improving the water resistance and heat resistance performance Is exhibited for the durable pest repellent.

As a pest repellent chemical that can be contained other than at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester, there can be cited dimethyl phthalate, dibutyl phthalate, 2-ethyl-1,3-hexanediol, di-n-propyl isocinchomeronate, p-dichlorobenzene, di-n-butyl succinate, carane-3,4-diol, 1-methylpropyl 2-(2-hydroxyethyl)-1-piperidinecarboxylate, p-menthane-3,8-diol, ethyl 3-(N-n-butyl-N-acetyl)aminopropionate ester, and p-menthane-3,8-diol. In the present invention, it is preferable that the total amount of N,N-diethyl-m-toluamide and 1-piperidinecarboxylic acid-2-(2-hydroxyethyl)-1-methylpropyl ester in the pest repellent chemicals is at least 50 mass %.

<Layered Silicate>

The layered silicate in the present invention comprises a specific component represented by Formula [1] below and can appropriately support within layers at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester, and also can support a large variety of pest repellent chemical within layers.

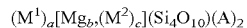

$$(M^1)_a[Mg_b,(M^2)_c](Si_4O_{10})(A)_2 \quad [1]$$

Here, ($M^1$) is Ca and/or Zn, ($M^2$) is Li and/or Na, and (A) means F and/or OH. At least part of (A) in Formula [1] is preferably F. Furthermore, $2a+2b+c=6$ and $0.001<c\le0.55$.

The layered silicate is a silicate in which crystalline layer units are superimposed on one another to form a layered structure, and there are natural products and synthetic products, which are different in terms of components and crystal structure as well as purity, particle size, etc. As specific layered silicates, there are many varieties such as the kaolin group, the smectite group, the talc-pyrophillite group, the vermiculite group, the mica group, the brittle mica group, the chlorite group, the serpentine group, and the interlayer-deficient mica group.

Among these layered silicate, only some in the smectite group such as beidellite, hectorite, or saponite and a synthetic fluorine mica in which part of the talc is replaced with fluorine and Na represented by Formula [1], can be used in the present invention.

As specific layered silicates that can be used in the present invention, there can be cited compounds represented by Formula [2] below in which components of various types of mica, eastonite, polylithionite, or celadonite are adjusted, and white substances represented by Formula [3] below in which components of hectorite, saponite, sauconite, stevensite, zinnwaldite, beidellite, nontronite, or volkonskoite are adjusted.

$(M)_a[Mg_b,(Na)_c](Si_4O_{10})F_2$   [2]

Here, ($M^1$) is Ca and/or Zn, $2a+2b+c=6$, and $0.001<c\le0.55$.

In Formula [2], a preferred value for a is $0.2<a<3$, and more preferably $0.22<a<0.3$. Furthermore, a preferred value for b is $2.3<b<2.8$, and more preferably $2.5<b<2.6$. A preferred value for c is $0.001<c<0.3$.

$(M^1)_a[Mg_b,(Li)_c](Si_4O_{10}(A)_2$   [3]

Here, ($M^1$) is Ca and/or Zn and (A) means F and/or OH. Furthermore, $2a+2b+c=6$ and $0.001<c\le0.55$.

In Formula [3], a preferred value for a is $0.2<a<3$, and more preferably $0.22<a<0.3$. Furthermore, a preferred value for b is $2.5<b<3$, and more preferably $2.55<b<2.58$. A preferred value for c is $0.15<c<0.5$, and more preferably 0.25 to 0.4. At least part of (A) in Formula [3] is preferably F.

With regard to the layered silicate, a natural product is a colored powder and when it is processed into a resin, etc. coloration occurs, and it is therefore preferably a synthetic product with a white or pale color.

Adjustment of components contained in the layered silicate may be carried out by ion exchange. A method for ion exchange is not particularly limited, and any conventionally known method may be used. For example, in order to increase the calcium ion content of a layered silicate, after it is immersed in an aqueous solution of water-soluble calcium such as calcium chloride, it is fully washed with deionized water or a solvent such as ethanol to thus increase the calcium ion content. By washing and removing exchangeable cations that are released after being replaced by calcium ion entering between layers of the layered silicate, the weather resistance and heat resistance of the durable pest repellent of the present invention are improved. That the progress of washing is sufficient can be found by measuring the electrical conductivity of the washing liquid. It is preferable to carry out washing until the electrical conductivity of the washing liquid becomes no greater than 509 μS/cm, more preferably no greater than 200 μS/cm, and yet more preferably no greater than 100 μS/cm. Furthermore, there is a method in which ion exchange is carried out by heating after the layered silicate is mixed with calcium carbonate, calcium nitrate, etc. In this case also, it is preferable to carry out washing.

The particle size, the water content, and the cation exchange capacity of the layered silicate in the present invention are not particularly limited. When it is used in kneading with a plastic, rubber, fiber, etc., a powder having an average particle size of no greater than 10 μm is preferable, a powder having an average particle size of 0.1 to 7 μm is more preferable, and it is preferable that the particle size distribution is small and the particle size is uniform. In order to exhibit a sufficient repellency effect when formed into a durable pest repellent, the cation exchange capacity is preferably at least 0.1 meq/g, and more preferably at least 0.5 meq/g. With regard to these layered silicates, only one type thereof may be used, but in order to control sustained release properties two or more types thereof may be used in combination.

The average particle size may be measured using for example a laser diffraction type particle size distribution analyzer after ultrasonically dispersing in deionized water, and it is usual to employ average particle size on a volume basis. The water content may easily be measured by the Karl-Fisher method, etc. The cation exchange capacity (usually abbreviated to CEC) is a value expressed as a milligram equivalent of exchangeable cations retained per fixed mass of a dried sample and may be determined by a known method such as for example an ammonium acetate solution leaching out method.

Only the layered silicate represented by Formula [1] in the present invention can appropriately retain between layers thereof at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester, the heat resistance and the solvent resistance of N,N-diethyl-m-toluamide, and N,N-diethyl-m-toluamide and/or 1-piperidinecarboxylic acid-2-(2-hydroxyethyl)-1-methylpropyl ester can be improved, and an effect of making the pest repellent effect long-lasting can be also exhibited. This appropriate retention can be controlled by the constituent components of the layered silicate and the interlayer spacing of the layered silicate after at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropylester is incorporated into the layers.

The above-mentioned interlayer spacing of the layered silicate after incorporation into the layers is preferably such that in a standard powder X-ray diffraction measurement using Cu Kα radiation, an (002) plane peak in a diffraction pattern is $2\theta=5.0°$ to 6.3° (meaning that the crystal plane distance d=14.0 to 17.7 angstroms), and more preferably 5.2 to 6.0° (meaning that the crystal plane distance d=14.7 to 17.0 angstroms). When the interlayer spacing is too narrow, it becomes difficult for any of N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester to be released, and a pest repellent effect cannot be sufficiently exhibited. On the other hand, when the interlayer spacing is too wide, it becomes easy for any of N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester to be released, and the heat resistance of the pest repellent is degraded, which is not desirable. The angstrom (Å) is a commonly used unit meaning a length of $10^{-10}$ m or 0.1 nm.

Since a large intensity for the peak indicating the interlayer spacing in X-ray diffraction means high uniformity of the layers and the presence of a large number of crystals having a certain interlayer spacing, the heat resistance of the pest repellent improves, which is desirable. In a powder X-ray diffraction pattern the X ray count for the (002) plane peak indicating the interlayer spacing of a layered silicate is preferably at least 1,000 cps under measurement conditions of 40 kV and 150 mA using a Cu tube, more preferably at least 5,000 cps, and yet more preferably at least 20,000 cps.

<Method for Supporting>

A method for supporting at least one of N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester on a specific layered silicate in the present invention is not particularly limited, and it can basically be carried out by uniformly mixing the layered silicate and at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester. Since any of N,N-diethyl-m-toluamide, 1-piperidinecarboxylic acid-2-(2-hydroxyethyl)-1-methylpropyl ester, and a mixture of N,N-diethyl-m-toluamide and 1-piperidinecarboxylic acid-2-(2-hydroxyethyl)-1-methylpropyl ester is a liquid at room temperature, supporting can be carried out by mixing with a layered silicate, stirring, then heating, and grinding. It is preferable to add a solvent at 0.5% to 5% of the layered silicate when carrying out mixing. The solvent is preferably water or an alcohol having no greater than 3 carbons, and more preferably water. Furthermore, at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester can be supported on a layered silicate by mixing and stirring a layered silicate with a solution of at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester, then filtering, drying, and grinding.

The larger the preferred amount of at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester supported on the layered silicate in the present invention, the larger the effect of pest repellency, but when the amount supported is too large, N,N-diethyl-m-toluamide and/or 1-piperidinecarboxylic acid-2-(2-hydroxyethyl)-1-methylpropyl ester that cannot be supported on the layered silicate might cause coloration, etc., and degrade the heat resistance. With regard to a preferred amount supported, the total amount of N,N-diethyl-m-toluamide and 1-piperidinecarboxylic acid-2-(2-hydroxyethyl)-1-methylpropyl ester per g of the layered silicate is 0.3 to 1.2 mmol, and more preferably 0.5 to 1.0 mmol.

The durable pest repellent of the present invention may use in combination an insecticide or a natural essential oil as long as the safety and durability are not impaired. Specific examples of the insecticide include 3-allyl-2-methylcyclopent-2-en-4-on-1-yl dl-cis/trans-chrysanthemate (product name Allethrin), 3-allyl-2-methylcyclopent-2-en-4-on-1-yl d-cis/trans-chrysanthemate (product name Pynamin Forte), d-3-allyl-2-methylcyclopent-2-en-4-on-1-yl d-trans-chrysanthemate (product name Exthrin), 3-allyl-2-methylcyclopent-2-en-4-on-1-yl d-trans-chrysanthemate (common name bioallethrin), N-(3,4,5,6-tetrahydrophthalimide)-methyl dl-cis/trans-chrysanthemate (common name phthalthrin), 5-benzyl-3-furylmethyl d-cis/trans-chrysanthemate (common name resmethrin), 5-(2-propargyl)-3-furylmethyl chrysanthemate (common name furamethrin), 3-phenoxybenzyl 2,2-dimethyl-3-(2',2'-dichloro)vinylcyclopropanecarboxylate (common name permethrin), 3-phenoxybenzyl d-cis/trans-chrysanthemate (common name phenothrin), α-cyano-3-phenoxybenzyl d-cis/trans-chrysanthemate, 1-ethynyl-2-methyl-pentenyl d-cis/trans-chrysanthemate (common name empenthrin), o-phenylphenol, sodium o-phenylphenol, p-t-octylphenol, 2-(4-ethoxyphenyl)-2-methylpropyl-3-phenoxybenzyl ether, thymol, diphenylthymol, chlorophen, paraben, alkylparaben, cresol, triclosan, Biosol, phenol, parachlorophenol, and chloroxylenol. Among them, permethrin, which also has pest repellency although it is weak, is preferable.

Specific examples of the natural essential oil that can be used in combination include cinnamon oil, thyme white oil, clove bud oil, cinnamon leaf oil, lavender French oil, lemongrass oil, peppermint oil, bergamot oil, tea tree oil, geranium oil, citronella oil, rose oil, lemon oil, eucalyptus oil, origanum oil, cinnamaldehyde, eugenol, methyl salicylate, citral, allyl isothiocyanate, benzyl isothiocyanate, phenylethyl isothiocyanate, linalool, menthol, geraniol, thymol, terpineol, and hinokitiol. Among them, eucalyptus oil is preferable, its active ingredient being known as PMD (p-menthane-3,8-diol).

At least one type of the above-mentioned insecticides or natural essential oils may be used as it is in a combination with the durable pest repellent of the present invention or may be used after being formed into a composite with the same support as in the present invention or another support; it is preferable for it to be supported within layers of the layered silicate as for at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester of the present invention, and in this case safety and durability will not be impaired. When the layered silicate affinity of one that is used in combination is much higher than that of at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester, if a large amount thereof is used in combination, the N,N-diethyl-m-toluamide and/or 1-piperidinecarboxylic acid-2-(2-hydroxyethyl)-1-methylpropyl ester supported within the layers might be pushed out, and it is essential for the total mass of chemicals used in combination to be smaller than at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester, and preferably no greater than ½.

The pest repellent resin composition can be obtained easily by formulating the durable pest repellent of the present invention with a resin. The type of resin that can be used is not particularly limited; it may be any of a natural resin, a synthetic resin, and a semi-synthetic resin, and it may be a thermoplastic resin or a thermosetting resin. As a specific resin, it may be any of a resin for molding, a resin for fiber, and a rubber resin, and examples thereof include resins for molding or fiber such as polyethylene, polypropylene, vinyl chloride, an ABS resin, an AS resin, an MBS resin, a nylon resin, polyester, polyvinylidene chloride, polystyrene, polyacetal, polycarbonate, PBT, an acrylic resin, a fluorine resin, a polyurethane elastomer, a polyester elastomer, a melamine, a urea resin, a tetrafluoroethylene resin, an unsaturated polyester resin, rayon, acetate, acrylic, polyvinyl alcohol, cupra, triacetate, and vinylidene, and rubber resins such as natural rubber, silicone rubber, styrene butadiene rubber, ethylene propylene rubber, fluorine rubber, nitrile rubber, chlorosulfonated polyethylene rubber, butadiene rubber, synthetic natural rubber, butyl rubber, urethane rubber, and acrylic rubber. It is also possible to prepare a pest repellent fiber by combining the durable pest repellent of the present invention with a fiber such as a natural fiber.

As a processing method for formulating the durable pest repellent of the present invention with a resin to form a pest repellent resin composition, any known method may be employed. For example, there are (1) a method in which a pellet-form resin or a powder-form resin is directly mixed in a mixer using an attachment agent for promoting attachment between the durable pest repellent powder and the resin or a dispersant for improving dispersibility of the pest repellent powder, (2) a method in which a mixture formed as above is molded into pellets by an extruder, and the molding is then formulated with a pellet-form resin, (3) a method in which a durable pest repellent is molded into high concentration pellets using a wax, and the pellet-form molding is then formulated with a pellet-form resin, (4) a method in which a paste-form composition is prepared by dispersing and mixing a durable pest repellent in a high viscosity liquid such as a polyol, and this paste is then formulated with a pellet-form resin, etc.

Molding of the above-mentioned pest repellent resin composition may employ any known processing technique and machine according to the properties of various types of resin, and preparation can easily be carried out by the method of mixing, incorporating, or kneading while heating and applying or reducing the pressure at an appropriate temperature and pressure; specific operations therefore may be carried out by a standard method, and molding can be carried out in various forms such as lump, sponge, film, sheet, fiber, pipe, or a composite thereof.

The durable pest repellent of the present invention may be formulated with a material and molded, and the shape of the molding can be made into any one of various shapes such as particles, fiber, film, sheet, plate, or block by a known molding method.

The higher the formulation ratio of the durable pest repellent of the present invention in the pest repellent resin composition, the better the persistence of the pest repellent, but when it is too much, resin properties such as molding strength are degraded, and it is therefore preferably 0.1 to 50 parts by weight relative to 100 parts by weight of the pest repellent resin composition, and more preferably 0.3 to 20 parts by weight.

<Application>

Specific applications of pest repellent products in which the durable pest repellent of the present invention is formulated include fiber products such as nets, carpets, curtains, screens, and clothing; leather; electrical appliances such as refrigerators, rice cookers, washing machines, dish dryers, vacuum cleaners, air conditioners, televisions, and telephones; building materials such as wall paper, tiles, bricks, concrete, screws, and joints; daily goods such as hanging wardrobes, tents, sheets, and dustbins; toiletry products; and various types of coating materials, paints, and adhesives.

Since the durable pest repellent of the present invention has high heat resistance, can be easily kneaded into a resin, and also has a persistent repellency effect, it is possible to impart to various resins an excellent repellent ability for a long period.

EXAMPLES

The present invention is explained more specifically below by reference to Examples and Comparative Examples.

Confirmation of the crystallinity of a layered silicate and whether or not at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester was supported between layers was carried out using a powder X-ray diffraction pattern obtained by a powder X-ray diffraction measurement using a powder X-ray diffractometer (model RINT2400V, Rigaku) with CuKα radiation under X ray conditions of 40 kV/150 mA. Under these measurement conditions, a diffraction peak appearing at $2\theta=5.0°$ to $6.3°$ indicates an (002) crystalline plane having an interlayer spacing with a plane distance of d=14.0 to 17.7 angstroms in the layered silicate.

<Measurement of Average Particle Size>

Measurement of particle size distribution and average particle size of a durable pest repellent was carried out by dispersing the durable pest repellent in deionized water, treating it with ultrasound at 70 W for at least 2 minutes, and then measuring using a laser diffraction type particle size distribution analyzer, the results being analyzed on a volumetric basis. The content % of the particle size distribution means volume % of the total particles from this analysis method, but since the density of the durable pest repellent is constant, it has the same meaning as that of mass %. Specifically, it was measured using 'MS2000' laser diffraction type particle size distribution measurement equipment made by Malvern Instruments, Ltd.

Reference Example 1

Preparation of Layered Silicate A 100.0 g of the sodium type fluorine-substituted synthetic mica $Na_{0.5}(Mg_{2.5}Na_{0.5})(Si_4O_{10})F_2$, which is a layered silicate, was added to 1.0 L of 0.1 mol/L concentration $CaCl_2$ aqueous solution, and stirring (300 rpm) was carried out at 60° C. for 4 hours so as to suspend it, thereby replacing ion exchangeable sodium ion of the layered silicate with calcium ion. The suspension thus obtained was washed with ion exchanged water until the electrical conductivity of the filtrate became no greater than 100 μS/cm, dried at 115° C. for 2 hours, and ground to give layered silicate A (structural formula: $Ca_{0.25}(Mg_{2.5}Na_{0.5})(Si_4O_{10})F_2$) having an average particle size of 5 μm.

Reference Example 2

Preparation of Layered Silicate B 100.0 g of the sodium type fluorine-substituted synthetic mica $Na_{0.5}(Mg_{2.5}Na_{0.5})(Si_4O_{10}F_2$, which is a layered silicate, was added to 1.0 L of 0.1 mol/L concentration $ZnCl_2$ aqueous solution, and stirring (300 rpm) was carried out at 60° C. for 4 hours so as to suspend it, thereby replacing ion exchangeable sodium ion of the layered silicate with zinc ion. The suspension thus obtained was washed with ion exchanged water until the electrical conductivity of the filtrate became no greater than 100 μS/cm, dried at 115° C. for 2 hours, and ground to give layered silicate B (structural formula: $Zn_{0.25}(Mg_{2.5}Na_{0.5})(Si_4O_{10})F_2$) having an average particle size of 5 μm.

Reference Example 3

Preparation of Layered Silicate C 100.0 g of the sodium type synthetic hectorite $Na_{0.33}(Mg_{2.67}Li_{0.33})(Si_4O_{10})(OH)_2$, which is a layered silicate, was added to 1.0 L of 0.1 mol/L concentration $CaCl_2$ aqueous solution, and stirring (300 rpm) was carried out at 60° C. for 4 hours so as to suspend it, thereby replacing ion exchangeable sodium ion of the layered silicate with calcium ion. The suspension thus obtained was washed with ion exchanged water until the electrical conductivity of the filtrate became no greater than 100 μS/cm, dried at 115° C. for 2 hours, and ground to give layered silicate C (structural formula: $Ca_{0.165}(Mg_{2.67}Li_{0.33})(Si_4O_{10}(OH)_2)$ having an average particle size of 6 μm.

Reference Example 4

Preparation of Layered Silicate D 100.0 g of the sodium type fluorine-substituted synthetic mica, which is a layered silicate, was added to 1.0 L of 0.1 mol/L concentration $MgCl_2.6H_2O$ aqueous solution, and stirring (300 rpm) was carried out at 60° C. for 4 hours so as to suspend it, thereby replacing ion exchangeable sodium ion of the layered silicate with magnesium ion. The suspension thus obtained was washed with ion exchanged water until the electrical conductivity of the filtrate became no greater than 100 μS/cm, dried at 115° C. for 2 hours, and ground to give layered silicate D (structural formula: $Mg_{0.25}(Mg_{2.5}Na_{0.5})(Si_4O_{10})F_2$) having an average particle size of 5 μm.

Reference Example 5

Preparation of Layered Silicate E 100.0 g of the sodium type fluorine-substituted synthetic mica, which is a layered silicate, was added to 1.0 L of 0.1 mol/L concentration $AlCl_3.6H_2O$ aqueous solution, and stirring (300 rpm) was carried out at 60° C. for 4 hours so as to suspend it, thereby replacing ion exchangeable sodium ion of the layered silicate with aluminum ion. The suspension thus obtained was washed with ion exchanged water until the electrical conductivity of the filtrate became no greater than 100 μS/cm, dried at 115° C. for 2 hours, and ground to give aluminum type layered silicate (structural formula: $Al_{0.5/3}(Mg_{2.5}Na_{0.5})(Si_4O_{10})F_2$) having an average particle size of 5 μm.

Reference Example 6

Preparation of Layered Silicate F 100.0 g of the purified montmorillonite (structural formula: $(Na, Ca)_{0.33}(Al_{1.67}Mg_{0.33})(Si_4O_{10})(OH)_2$), which is a layered silicate, was added to 1.0 L of 0.1 mol/L concentration $CaCl_2$ aqueous solution, and stirring (300 rpm) was carried out at 60° C. for 4 hours so as to suspend it, thereby replacing ion exchangeable sodium ion of the layered silicate with calcium ion. The suspension thus obtained was washed with ion exchanged water until the electrical conductivity of the filtrate became no greater than 100 μS/cm, dried at 115° C. for 2 hours, and ground to give calcium type layered silicate F (structural formula: $Ca_{0.165}(Al_{1.67}Mg_{0.33})(Si_4O_{10}(OH)_2)$) having an average particle size of 2 μm.

Reference Example 7

Preparation of Layered Silicate J 100.0 g of the purified montmorillonite (structural formula: $(Na)_{0.33}Mg_3(Si_{3.67}Al_{0.33}O_{10})(OH)_2$), which is a layered silicate, was added to 1.0 L of 0.1 mol/L concentration $CaCl_2$ aqueous solution, and stirring (300 rpm) was carried out at 60° C. for 4 hours so as to suspend it, thereby replacing ion exchangeable sodium ion of the layered silicate with calcium ion. The suspension thus obtained was washed with ion exchanged water until the electrical conductivity of the filtrate became no greater than 100 μS/cm, dried at 115° C. for 2 hours, and ground to give calcium type layered silicate J (structural formula: $Ca_{0.165}Mg_3(Si_{3.67}Al_{0.33}O_{10})(OH)_2$) having an average particle size of 7 μm.

Example 1-1

Durable pest repellent 1-1 was obtained by adding 0.2 g of deionized water and 0.32 g (2 mmol) of N,N-diethyl-m-toluamide to 10.0 g of layered silicate A obtained in Reference Example 1, and mixing well using a mortar. A powder X-ray diffraction was measured and it was found that there was a peak at 2θ=6.74° (d=13.1 angstroms) having an intensity of 16000 cps.

Nitrogen content was determined from the analytical results of the gas obtained by burning durable pest repellent 1-1 at 950° C. in oxygen/He mixed gas using a CHN elemental analyzer (model MT-5, Yanagimoto Seisakujo); when it was assumed that the nitrogen content was derived from N,N-diethyl-m-toluamide and calculation was carried out by multiplying by the molecular weight, the amount of N,N-diethyl-m-toluamide supported was 3.0 mass %, and it coincided with the amount supported calculated from the amount added.

Figure 3:
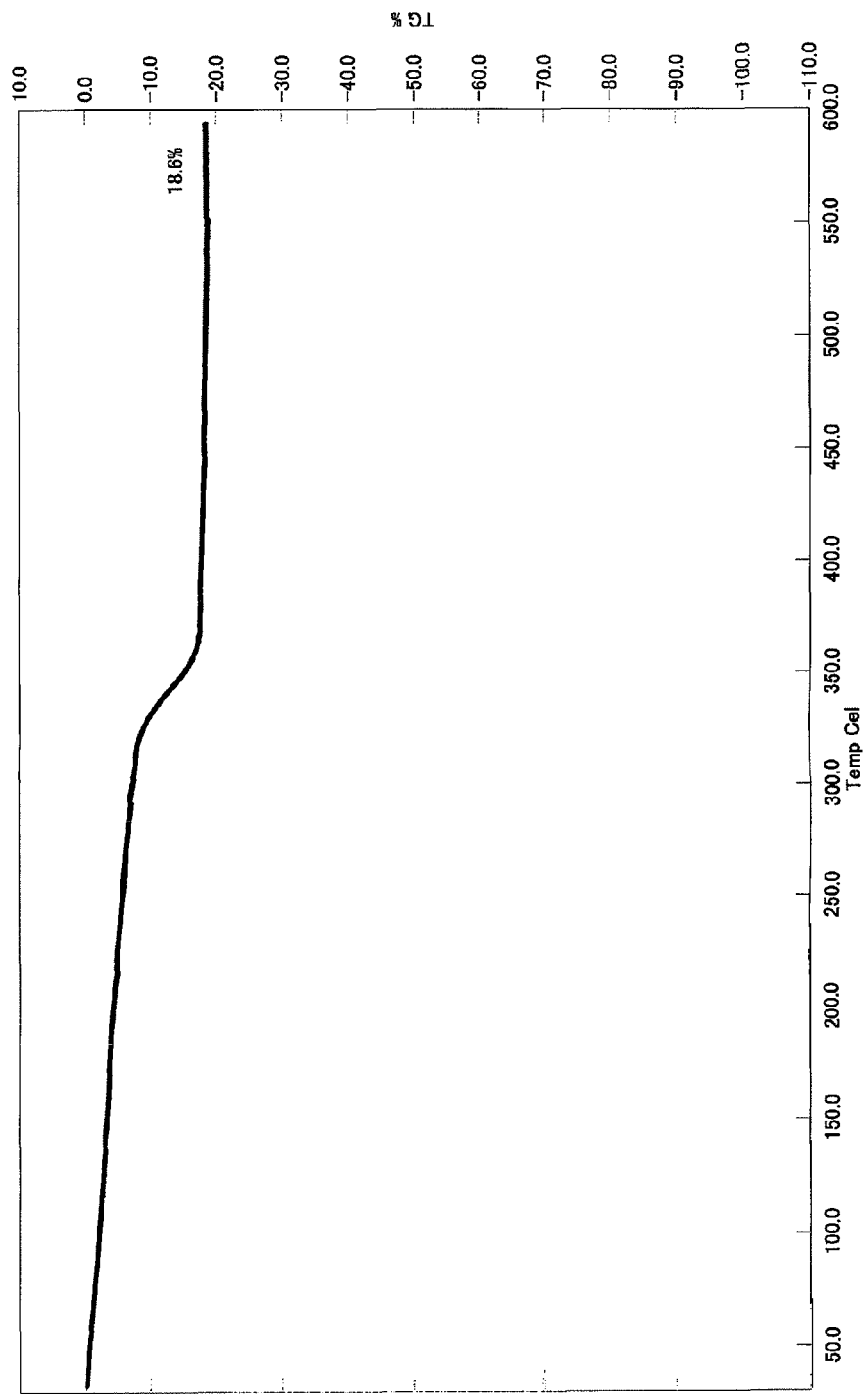
FIG. 3: A thermal analysis measurement chart showing thermogravimetric change of durable pest repellent 1-8 obtained in Example 1-8.

Furthermore, it was confirmed by thermal analysis that the supported N,N-diethyl-m-toluamide acquired heat resistance. The thermal analysis was carried out using a Model TG/DTA220 manufactured by Seiko Instruments under an air atmosphere, the measurement temperature was 30° C. to 600° C., and the rate of temperature increase was 20° C./min. Since the measurement is carried out in air, the overall heat resistance in air including vaporization and oxidative decomposition can be evaluated, and N,N-diethyl-m-toluamide that only adheres to the surface of a porous substance having a large specific surface area is subjected to oxidative decomposition at relatively low temperature and the weight decreases, whereas it is expected that N,N-diethyl-m-toluamide that is packed between layers of the inorganic layered compound without gaps is resistant to vaporization and oxidative decomposition and the weight will be maintained up to a higher temperature. For example, as is clear from a comparison between FIG. 3 and FIG. 4, even looking only at the temperature of the inflection point at which the supported chemical is rapidly lost makes it clear that the heat resistance of the durable pest repellent of the present invention is higher, but in order to make the comparison easier with figures, the temperature at which the amount of supported chemical component has been reduced by ⅓ is read off from the measurement results of the thermal analysis, defined as the 'heat resistance', and is shown in Table 1.

Example 1-2

Durable pest repellent 1-2 was obtained by adding 0.2 g of deionized water and 0.53 g (3 mmol) of N,N-diethyl-m-toluamide to 10.0 g of layered silicate A obtained in Reference Example 1 and mixing well using a mortar. When a powder X-ray diffraction was measured, it was found that there was a peak at 2θ=5.82° (d=15.2 angstroms) with an intensity of 22500 cps. When the nitrogen content was measured in the same manner as in Example 1-1 using a CHN elemental analyzer and the amount of N,N-diethyl-m-toluamide supported was calculated, it was found to be 5.0 mass %, and it coincided with the amount supported calculated from the amount added. Furthermore, a figure for the heat resistance was obtained by carrying out a thermal analysis and is shown in Table 1.

Example 1-3

Durable pest repellent 1-3 was obtained by adding 0.2 g of deionized water and 1.1 g (6 mmol) of N,N-diethyl-m-toluamide to 10.0 g of layered silicate A obtained in Reference Example 1 and mixing well using a mortar. When a powder X-ray diffraction was measured, it was found that there was a peak at 2θ=5.82° (d=15.2 angstroms) with an intensity of 44000 cps. When the nitrogen content was measured in the same manner as in Example 1-1 using a CHN elemental analyzer and the amount of N,N-diethyl-m-toluamide supported was calculated, it was found to be 10.0 mass %, and it coincided with the amount supported calculated from the amount added. Furthermore, a figure for the heat resistance was obtained by carrying out a thermal analysis and is shown in Table 1.

Example 1-4

Durable pest repellent 1-4 was obtained by adding 0.2 g of deionized water and 1.7 g (9 mmol) of N,N-diethyl-m-toluamide to 10.0 g of layered silicate A obtained in Reference Example 1 and mixing well using a mortar. When a powder X-ray diffraction was measured, it was found that there was a peak at 2θ=5.82° (d=15.2 angstroms) with an intensity of 66000 cps. When the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. Furthermore, a figure for the heat resistance was obtained by carrying out a thermal analysis and is shown in Table 1.

Example 1-5

Durable pest repellent 1-5 was obtained by adding 0.2 g of deionized water and 2.1 g (13 mmol) of N,N-diethyl-m-toluamide to 10.0 g of layered silicate A obtained in Reference Example 1 and mixing well using a mortar. When a powder X-ray diffraction was measured, it was found that there was a peak at 2θ=4.74° (d=18.6 angstroms) with an intensity of 79000 cps. When the nitrogen content was measured in the same manner as in Example 1-1 using a CHN elemental analyzer and the amount of N,N-diethyl-m-toluamide supported was calculated, it was found to be 20.0 mass %, and it coincided with the amount supported calculated from the amount added. Furthermore, a figure for the heat resistance was obtained by carrying out a thermal analysis and is shown in Table 1.

Example 1-6

Durable pest repellent 1-6 was obtained by adding 0.5 g of ethanol and 1.1 g (6 mmol) of N,N-diethyl-m-toluamide to 10.0 g of layered silicate A obtained in Reference Example 1, mixing well using a mortar, and drying at 90° C. for 1 hour. When a powder X-ray diffraction was measured, it was found that there was a peak at 2θ=5.82° (d=15.2 angstroms) with an intensity of 23500 cps. When the nitrogen content was measured in the same manner as in Example 1-1 using a CHN elemental analyzer and the amount of N,N-diethyl-m-toluamide supported was calculated, it was found to be 10.0 mass %, and it coincided with the amount supported calculated from the amount added. Furthermore, a figure for the heat resistance was obtained by carrying out a thermal analysis and is shown in Table 1.

Example 1-7

Durable pest repellent 1-7 was obtained by adding 0.2 g of deionized water and 1.1 g (6 mmol) of N,N-diethyl-m-toluamide to 10.0 g of layered silicate B obtained in Reference Example 2 and mixing well using a mortar. When a powder X-ray diffraction was measured, it was found that there was a peak at 2θ=5.74° (d=15.4 angstroms) with an intensity of 70000 cps. When the nitrogen content was measured in the same manner as in Example 1-1 using a CHN elemental analyzer and the amount of N,N-diethyl-m-toluamide supported was calculated, it was found to be 10.0 mass %, and it coincided with the amount supported calculated from the amount added. Furthermore, a figure for the heat resistance was obtained by carrying out a thermal analysis and is shown in Table 1.

Example 1-8

Durable pest repellent 1-8 was obtained by adding 0.2 g of deionized water and 1.7 g (9 mmol) of N,N-diethyl-m-toluamide to 10.0 g of layered silicate B obtained in Reference Example 2 and mixing well using a mortar. When a powder X-ray diffraction was measured, it was found that there was a peak at 2θ=5.74° (d=15.4 angstroms) with an intensity of 66000 cps. When the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. Furthermore, a figure for the heat resistance was obtained by carrying out a thermal analysis and is shown in Table 1.

Example 1-9

Durable pest repellent 1-9 was obtained by adding 0.2 g of deionized water and 2.1 g (13 mmol) of N,N-diethyl-m-toluamide to 10.0 g of layered silicate B obtained in Reference Example 2 and mixing well using a mortar. When a powder X-ray diffraction was measured, it was found that there was a peak at 2θ=5.04° (d=17.5 angstroms) with an intensity of 32000 cps. When the nitrogen content was measured in the same manner as in Example 1-1 using a CHN elemental analyzer and the amount of N,N-diethyl-m-toluamide supported was calculated, it was found to be 20.0 mass %, and it coincided with the amount supported calculated from the amount added. Furthermore, a figure for the heat resistance was obtained by carrying out a thermal analysis and is shown in Table 1.

Example 1-10

Durable pest repellent 1-10 was obtained by adding 0.2 g of deionized water and 1.7 g (9 mmol) of N,N-diethyl-m-toluamide to 10.0 g of layered silicate C obtained in Reference Example 3 and mixing well using a mortar. When a powder X-ray diffraction was measured, it was found that there was a peak at $2\theta=5.36°$ (d=16.5 angstroms) with an intensity of 1700 cps. When the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. Furthermore, a figure for the heat resistance was obtained by carrying out a thermal analysis and is shown in Table 1.

Comparative Example 1-1

Figure 4:
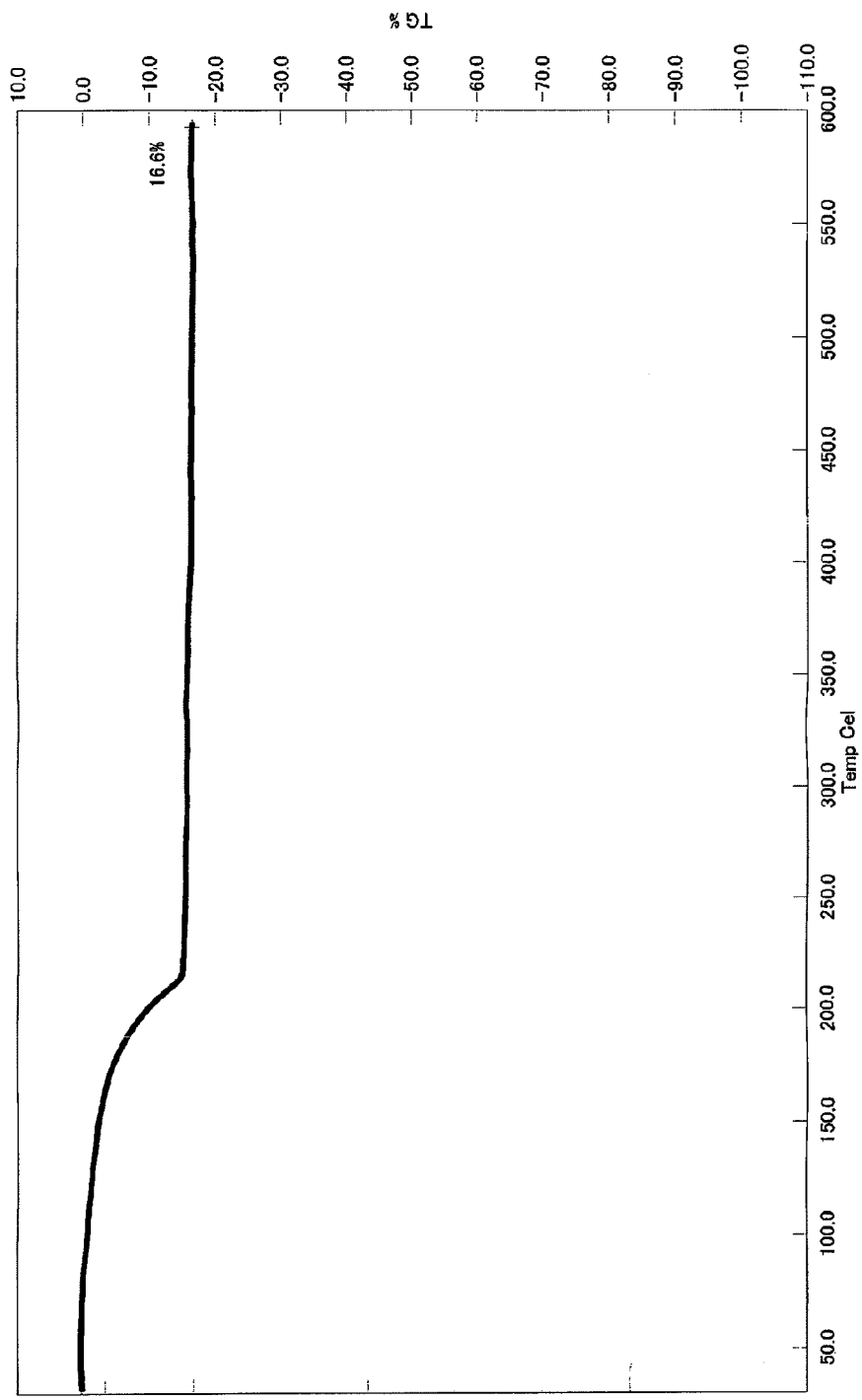
FIG. 4: A thermal analysis measurement chart showing thermogravimetric change of comparative pest repellent 1-1 obtained in Comparative Example 1-1.
Figure 5:
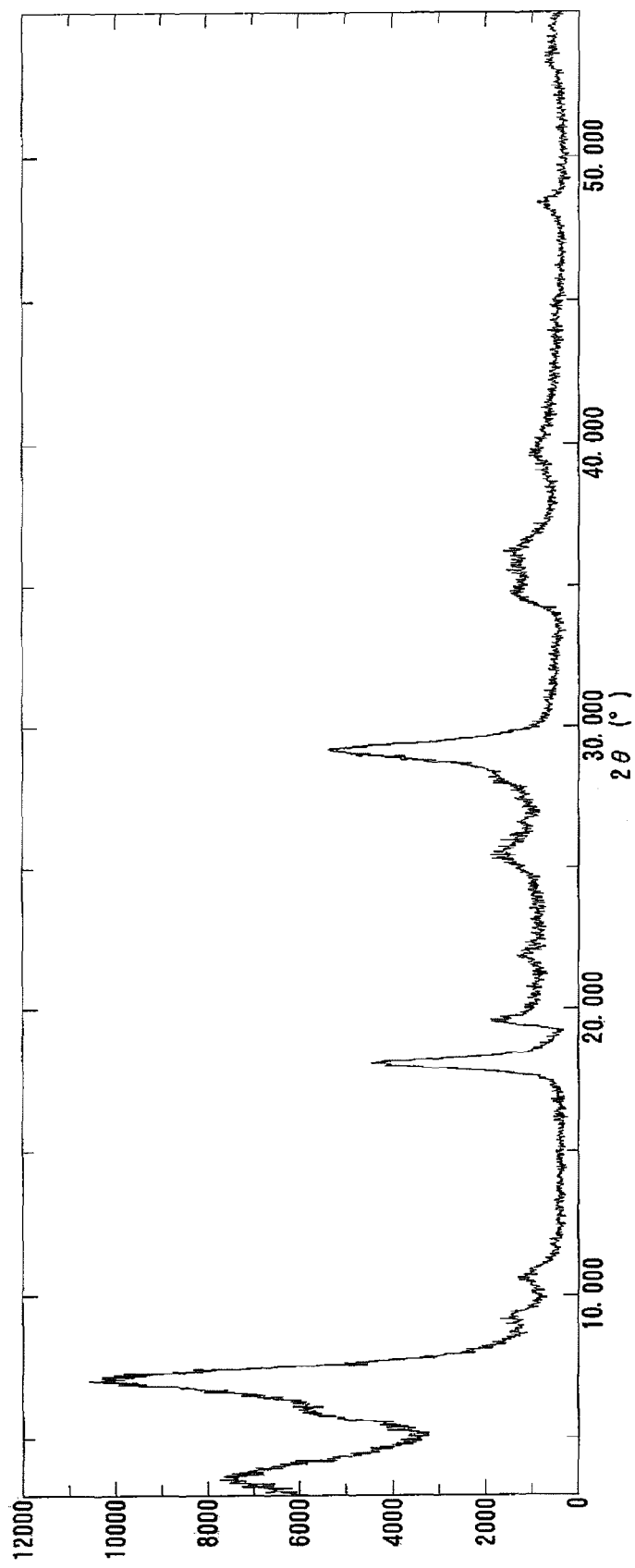
FIG. 5: A powder X-ray diffraction pattern of durable pest repellent 2-1 obtained in Example 2-1.
Figure 6:
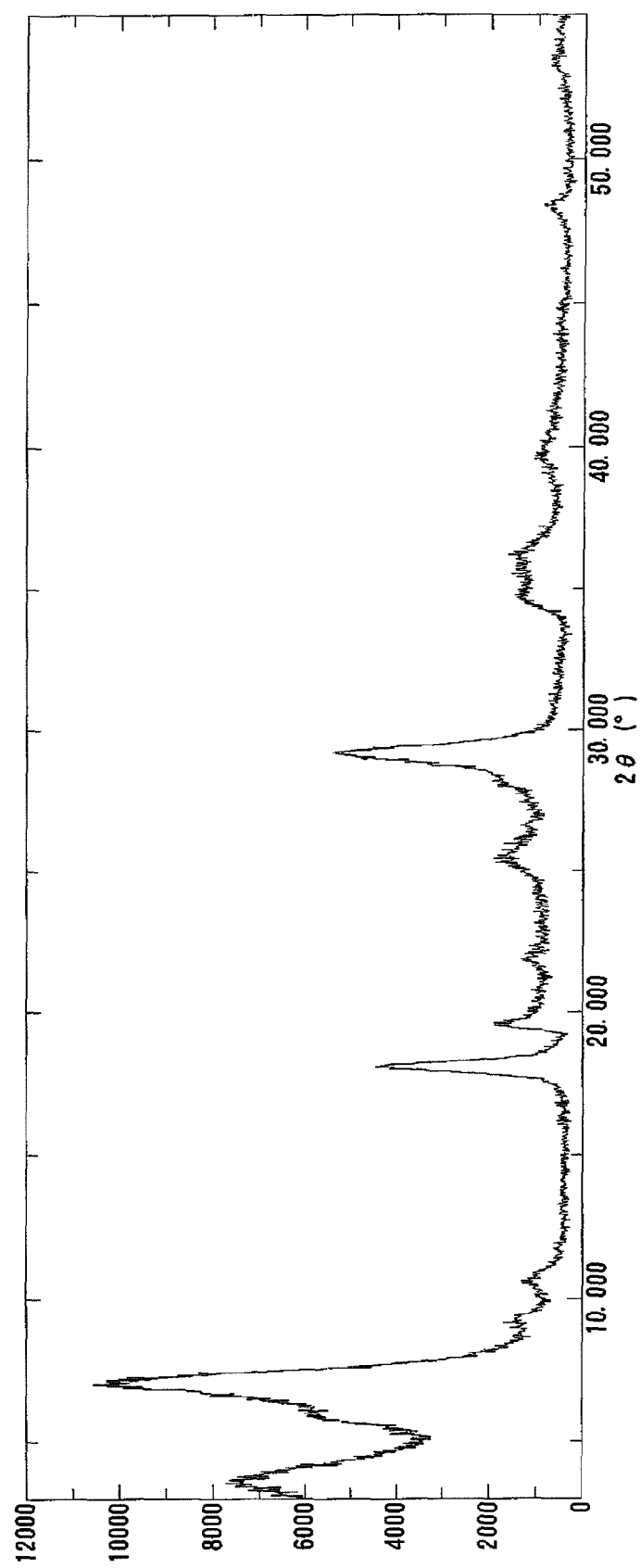
FIG. 6: A powder X-ray diffraction pattern of comparative pest repellent 2-1 obtained in Comparative Example 2-1.

Comparative pest repellent 1-1 was obtained by adding 1.7 g (9 mmol) of N,N-diethyl-m-toluamide to 10.0 g of the layered silicate A obtained in Reference Example 1, and mixing well using a mortar. When a powder X-ray diffraction was measured, it was found that there was a peak at $2\theta=7.06°$ (d=12.5 angstroms) with an intensity of 12000 cps. The value for d is the same as the result of powder X ray measurement for layered silicate A before adding N,N-diethyl-m-toluamide, suggesting that the added N,N-diethyl-m-toluamide did not enter between the layers of layered silicate A at all. However, when the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. This suggests that N,N-diethyl-m-toluamide adheres to on the surface of layered silicate A. Furthermore, a figure for the heat resistance was obtained by carrying out a thermal analysis and is shown in Table 1. A chart of the thermal analysis is shown in FIG. 4; there is a clear difference compared with the thermal analysis chart (FIG. 3) of Example 1-8 with an amount supported of 15%, which is the same as above, and there is also a difference in value for the heat resistance in Table 1.

Comparative Example 1-2

Comparative pest repellent 1-2 was obtained by adding 0.5 g of hexane and 1.7 g (9 mmol) of N,N-diethyl-m-toluamide to 10.0 g of the layered silicate A obtained in Reference Example 1, mixing well using a mortar, and drying at 90° C. for 2 hours. When a powder X-ray diffraction was measured, it was found that there was a peak at $2\theta=7.06°$ (d=12.5 angstroms) with an intensity of 5000 cps. The value for d is the same as the result of powder X ray measurement for layered silicate A before adding N,N-diethyl-m-toluamide, suggesting that the added N,N-diethyl-m-toluamide did not enter between the layers of layered silicate A at all. However, when the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. This suggests that N,N-diethyl-m-toluamide adheres to on the surface of layered silicate A. Furthermore, a figure for the heat resistance was obtained by carrying out a thermal analysis and is shown in Table 1.

Comparative Example 1-3

Comparative pest repellent 1-3 was obtained by adding 0.2 g of deionized water and 1.7 g (9 mmol) of N,N-diethyl-m-toluamide to 10.0 g of sodium type fluorine-substituted synthetic mica (Somasif ME-100: $NaMg_{2.5}(Si_4O_{10})F_2$) manufactured by Co-op Chemical Co., Ltd.) which is a layered silicate, and mixing well using a mortar. When a powder X-ray diffraction was measured, it was found that there was a peak at $2\theta=7.06°$ (d=12.5 angstroms) with an intensity of 2000 cps. When the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. Furthermore, a figure for the heat resistance was obtained by carrying out a thermal analysis and is shown in Table 1.

Comparative Example 1-4

Comparative pest repellent 1-4 was obtained by adding 0.2 g of deionized water and 1.7 g (9 mmol) of N,N-diethyl-m-toluamide to 10.0 g of the layered silicate D obtained in Reference Example 4, and mixing well using a mortar. When a powder X-ray diffraction was measured, it was found that there was a peak at $2\theta=5.04°$ (d=17.5 angstroms) with an intensity of 12000 cps. The value for d is the same as the result of powder X ray measurement for layered silicate D before adding N,N-diethyl-m-toluamide, suggesting that the added N,N-diethyl-m-toluamide did not enter between the layers of layered silicate D at all. However, when the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. Furthermore, a figure for the heat resistance was obtained by carrying out a thermal analysis and is shown in Table 1.

Comparative Example 1-5

Comparative pest repellent 1-5 was obtained by adding 0.2 g of deionized water and 1.7 g (9 mmol) of N,N-diethyl-m-toluamide to 10.0 g of the layered silicate E obtained in Reference Example 5, and mixing well using a mortar. When a powder X-ray diffraction was measured, it was found that there was a peak at $2\theta=5.66°$ (d=15.6 angstroms) with an intensity of 12000 cps. The value for d is the same as the result of powder X ray measurement for layered silicate E before adding N,N-diethyl-m-toluamide, suggesting that the added N,N-diethyl-m-toluamide did not enter between the layers of layered silicate E at all. However, when the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. Furthermore, a figure for the heat resistance was obtained by carrying out a thermal analysis and is shown in Table 1.

Comparative Example 1-6

Comparative pest repellent 1-6 was obtained by adding 0.2 g of deionized water and 1.7 g (9 mmol) of N,N-diethyl-m-toluamide to 10.0 g of the layered silicate F obtained in Reference Example 6, and mixing well using a mortar. When a powder X-ray diffraction was measured, it was found that there was a peak at 2θ=5.8° (d=15.2 angstroms) with an intensity of 68000 cps. The value for d is the same as the result of powder X ray measurement for layered silicate F before adding N,N-diethyl-m-toluamide, suggesting that the added N,N-diethyl-m-toluamide did not enter between the layers of layered silicate F at all. However, when the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. Furthermore, a figure for the heat resistance was obtained by carrying out a thermal analysis and is shown in Table 1.

Comparative Example 1-7

Comparative pest repellent 1-7 was obtained by adding 0.2 g of deionized water and 1.7 g (9 mmol) of N,N-diethyl-m-toluamide to 10.0 g of the layered silicate J obtained in Reference Example 7, and mixing well using a mortar. When a powder X-ray diffraction was measured, it was found that there was a peak at 2θ=5.16° (d=17.1 angstroms) with an intensity of 900 cps. The value for d is the same as the result of powder X ray measurement for layered silicate J before adding N,N-diethyl-m-toluamide, suggesting that the added N,N-diethyl-m-toluamide did not enter between the layers of layered silicate J at all. However, when the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. Furthermore, a figure for the heat resistance was obtained by carrying out a thermal analysis and is shown in Table 1.

Comparative Example 1-8

Comparative pest repellent 1-8 was obtained by adding 0.2 g of deionized water and 1.7 g (9 mmol) of N,N-diethyl-m-toluamide to 10.0 g of silica gel, and mixing well using a mortar. For comparative pest repellent 1-8, a powder X-ray diffraction measurement was not carried out, but when the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. Furthermore, a figure for the heat resistance was obtained by carrying out a thermal analysis and is shown in Table 1.

Comparative Example 1-9

A Y-type zeolite ($Na_{0.58}Al_{0.58}Si_{1.34}O_{3.84} \cdot 2.5H_2O$) was heated at 350° C. for 24 hours and allowed to stand under nitrogen until it reached normal temperature. Comparative pest repellent 1-9 was obtained by adding 1.7 g (9 mmol) of N,N-diethyl-m-toluamide to 10.0 g of the above and mixing well using a mortar. For comparative pest repellent 1-9, a powder X-ray diffraction measurement was not carried out, but when the nitrogen content was measured in the same manner as in Example 1-1 using a CHN elemental analyzer and the amount of N,N-diethyl-m-toluamide supported was calculated, it was found to be 30.0 mass %, and it coincided with the amount supported calculated from the amount added. Furthermore, a figure for the heat resistance was obtained by carrying out a thermal analysis and is shown in Table 1.

Comparative Example 1-10

A synthetic hydrotalcite ($Mg_{2.5}Al_2(OH)_{13} \cdot CO_3 \cdot mH_2O$) was heated at 350° C. for 24 hours and allowed to stand under nitrogen until it reached normal temperature. Comparative pest repellent 1-10 was obtained by adding 1.7 g (9 mmol) of N,N-diethyl-m-toluamide to 10.0 g of the above and mixing well using a mortar. For comparative pest repellent 1-10, a powder X-ray diffraction measurement was not carried out, but when the nitrogen content was measured in the same manner as in Example 1-1 using a CHN elemental analyzer and the amount of N,N-diethyl-m-toluamide supported was calculated, it was found to be 30.0 mass %, and it coincided with the amount supported calculated from the amount added. Furthermore, a figure for the heat resistance was obtained by carrying out a thermal analysis and is shown in Table 1.

Comparative Example 1-11

Comparative pest repellent 1-11 was obtained by adding 0.2 g of deionized water and 1.7 g (9 mmol) of N,N-diethyl-m-toluamide to 10.0 g of an aluminum silicate (Kyowaad 700 manufactured by Kyowa Chemical Industry Co., Ltd.: $Al_2O_3 \cdot 9SiO_2 \cdot H_2O$) and mixing well using a mortar. For comparative pest repellent 1-11, a powder X-ray diffraction measurement was not carried out, but when the nitrogen content was measured in the same manner as in Example 1-1 using a CHN elemental analyzer and the amount of N,N-diethyl-m-toluamide supported was calculated, it was found to be 15.0 mass %, and it coincided with the amount supported calculated from the amount added. Furthermore, a figure for the heat resistance was obtained by carrying out a thermal analysis and is shown in Table 1.

Comparative Example 1-12

0.4 g of α-cyano-3-phenoxybenzyl d-cis/trans-chrysanthemate, which is a pyrethroid compound, and 30 g of polyoxyethylene octyl ether were dissolved in 100 mL of deionized water, 1 g of α-zirconium phosphate, which is an inorganic layered compound, was added thereto, and shaking was then carried out at 40° C. for 48 hours. Subsequently, a solid phase was separated by filtration, washed with deionized water to remove unreacted chemical, and then dried at 150° C. for 2 hours, thus giving comparative pest repellent 1-12 in which 23 mass % of α-cyano-3-phenoxybenzyl d-cis/trans-chrysanthemate was supported on α-zirconium phosphate. For comparative pest repellent 1-12, a powder X-ray diffraction measurement was not carried out, but when the nitrogen content was measured in the same manner as in Example 1-1 using a CHN elemental analyzer and the amount of N,N-diethyl-m-toluamide supported was calculated, it was found to be 23.0 mass %, and it coincided with the amount supported calculated from the amount added. Furthermore, a figure for the heat resistance was obtained by carrying out a thermal analysis and is shown in Table 1.

Comparative Example 1-13

0.4 g of α-cyano-3-phenoxybenzyl d-cis/trans-chrysanthemate, which is the same as in Comparative Example 1-12, was dissolved in 100 mL of dimethyl sulfide, 1 g of a copper-substituted α-zirconium phosphate containing 13% by weight of copper was added thereto, and shaking was then carried out at 40° C. for 48 hours. Subsequently, a solid phase was separated by filtration and washed with dimethyl sulfide to remove unreacted chemical, then dried at 150° C. for 2 hours, thus giving comparative pest repellent 1-13 in which 20 mass % of α-cyano-3-phenoxybenzyl d-cis/trans-chrysanthemate was supported on copper type zirconium phosphate. For comparative pest repellent 1-13, a powder X-ray diffraction measurement was not carried out, but when the nitrogen content was measured in the same manner as in Example 1-1 using a CNN elemental analyzer and the amount of N,N-diethyl-m-toluamide supported was calculated, it was found to be 20.0 mass %, and it coincided with the amount supported calculated from the amount added. Furthermore, a figure for the heat resistance was obtained by carrying out a thermal analysis and is shown in Table 1.

Comparative Example 1-14

7.5 g of 1-ethynyl-2-methyl-pentenyl d-cis/trans-chrysanthemate as a pyrethroid compound was added to 42.5 g of the layered silicate A obtained in Reference Example 1, mixed using a ball mill for 24 hours, then heated at 120° C. for 2 hours, and then cooled to room temperature. A complex thus obtained was washed with acetonitrile and dried under vacuum at 100° C., thus giving comparative pest repellent 1-14 containing 11 mass % of 1-ethynyl-2-methyl-pentenyl d-cis/trans-chrysanthemate. When a powder X-ray diffraction was measured, it was found that there was a peak at $2\theta=7.06°$ (d=12.5 angstroms) with an intensity of 10000 cps. The value for d is the same as the result of powder X ray measurement for layered silicate A before adding 1-ethynyl-2-methyl-pentenyl d-cis/trans-chrysanthemate, suggesting that the 1-ethynyl-2-methyl-pentenyl d-cis/trans-chrysanthemate added did not enter between the layers of layered silicate A at all. When the nitrogen content was measured in the same manner as in Example 1-1 using a CHN elemental analyzer and the amount of N,N-diethyl-m-toluamide supported was calculated, it was found to be 11.0 mass %, and it coincided with the amount supported calculated from the amount added. Furthermore, a figure for the heat resistance was obtained by carrying out a thermal analysis and is shown in Table 1.

Comparative Reference Example 1-1

In Comparative Reference Example 1-1, N,N-diethyl-m-toluamide was used as the pest repellent chemical. N,N-Diethyl-m-toluamide is a liquid, an inorganic substance was not used in combination, and powder X-ray diffraction measurement was therefore not carried out. Furthermore, a figure for the heat resistance was obtained by carrying out a thermal analysis, and the result is shown in Table 1.

<Evaluation of Resin Moldability>

The durable pest repellents prepared in Examples 1-1 to 1-10, and the comparative pest repellents prepared in Comparative Examples 1-1 to 1-14 and Comparative Reference Example 1-1 were mixed with a polyethylene resin (PE-NUC-8350, Nippon Unicar Co., Ltd.). For example, in the durable pest repellent of Example 1-1, since the amount of pest repellent chemical supported was 3 mass %, when the amount of repellent added in a resin composition shown in Table 2 was 5%, the amount of pest repellent chemical added was calculated as 0.15 mass %, and when the amount of repellent added in the resin composition was 10%, the amount of pest repellent chemical added was calculated as 0.3 mass %.

Resin compositions were produced by adjusting the amount of each repellent added to the resin composition so that the amount of pest repellent chemical added in the resin composition was 0.3 mass %, 0.15%, and 0.6%, they were injection-molded into flat plates, and evaluation of whether kneading into the resin was possible was carried out. Molding was carried out using a Model M-50A(II)-DM manufactured by Meiki Co., Ltd. at a molding temperature of 250° C., thus giving 10 cm square plates having a thickness of 2 mm. Furthermore, the residence time was 5 minutes, and checks as to whether or not there was foaming, a strange smell, or discoloration during molding were carried out. The results are shown in Table 2.

With regard to the pest repellent resin compositions prepared in Comparative Examples 1-12 to 1-14, molding was carried out after they were added to a polyethylene resin at 0.3% as a pest repellent chemical, and evaluation was carried out in the same manner. A plate was molded without adding any chemical and defined as Comparative Reference Example 1-2.

<Evaluation of Repellency>

Plates molded after adding the pest repellents prepared in Examples 1-1 to 1-10 and Comparative Examples 1-1 to 1-14 and Comparative Reference Example 1-1 to a polyethylene resin (PE-NUC-8350 manufactured by Nippon Unicar Co., Ltd.) so that the pest repellent chemical was 0.3 mass % of the entire resin composition were cut into circles having a diameter of a little under 4 cm and subjected to a test for anti-mite properties. The test was carried by an intrusion-prevention method in accordance with JIS L 1920 'Testing methods for efficacy against house dust mite of textiles'. The results (percentage repellency) of the test for anti-mite properties are shown in Table 2.

<Evaluation of Persistence of Repellence>

Plates molded after adding the pest repellents prepared in Examples 1-1 to 1-10 and Comparative Examples 1-1 to 1-14 and Comparative Reference Example 1-1 to a polyethylene resin (PE-NUC-8350 manufactured by Nippon Unicar Co., Ltd.) so that the pest repellent component was 0.3 mass % were held in a dryer at 81° C. for 48 hours. They were cut into circles having a diameter of a little under 4 cm and subjected to a test for anti-mite properties. The test was carried by an intrusion-prevention method in accordance with JIS L 1920 'Testing methods for efficacy against house dust mite of textiles'. The results (percentage repellency) of the test for anti-mite properties are shown in Table 2.

<Evaluation of Water Resistant Persistence of Repellence>

Flat plates were injection-molded using pest repellent resin compositions obtained by adding the pest repellents prepared in Examples 1-1 to 1-10 and Comparative Examples 1-1 to 1-14 and Comparative Reference Example 1-1 to a polyethylene resin (PE-NUC-8350, Nippon Unicar Co., Ltd.) at 0.3 mass %. The flat plate was immersed in hot water at 50° C. for 16 hours to thus carry out a water resistant persistence test. The flat plate after the test was cut into a disc having a diameter of a little under 4 cm and subjected to a test for anti-mite properties. The test was carried by an intrusion-prevention method in accordance with JIS L 1920 'Testing methods for efficacy against house dust mite of textiles'. The results (percentage repellency) of the test for anti-mite properties are shown in Table 2.

<Properties of Pest Repellents>

TABLE 1

|  | Solvent and amount added | Peak due to (002) plane 2θ (°) | Plane distance of (002) plane d (Å) | Peak intensity of (002) plane (cps) | Heat resistance (° C.) |
|---|---|---|---|---|---|
| Example 1-1 | Water 2% | 6.74 | 13.1 | 16000 | 250 |
| Example 1-2 | Water 2% | 5.82 | 15.2 | 22500 | 235 |
| Example 1-3 | Water 2% | 5.82 | 15.2 | 44000 | 241 |
| Example 1-4 | Water 2% | 5.82 | 15.2 | 66000 | 247 |
| Example 1-5 | Water 2% | 4.74 | 18.6 | 79000 | 205 |
| Example 1-6 | Ethanol 5% | 5.8 | 15.2 | 23500 | 237 |
| Example 1-7 | Water 2% | 5.74 | 15.4 | 70000 | 311 |
| Example 1-8 | Water 2% | 5.74 | 15.4 | 66000 | 302 |
| Example 1-9 | Water 2% | 5.04 | 17.5 | 32000 | 210 |
| Example 1-10 | Water 2% | 5.36 | 16.5 | 1700 | 239 |
| Comp. Ex. 1-1 | None | 7.06 | 12.5 | 12000 | 147 |
| Comp. Ex. 1-2 | Hexane 5% | 7.06 | 12.5 | 5000 | 152 |
| Comp. Ex. 1-3 | Water 2% | 7.06 | 12.5 | 2000 | 155 |
| Comp. Ex. 1-4 | Water 2% | 5.04 | 17.5 | 12000 | 178 |
| Comp. Ex. 1-5 | Water 2% | 5.66 | 15.6 | 12000 | 230 |
| Comp. Ex. 1-6 | Water 2% | 5.8 | 15.2 | 68000 | 236 |
| Comp. Ex. 1-7 | Water 2% | 5.16 | 17.1 | 900 | 189 |
| Comp. Ex. 1-8 | None | — | — | — | 191 |
| Comp. Ex. 1-9 | None | — | — | — | 160 |
| Comp. Ex. 1-10 | None | — | — | — | 158 |
| Comp. Ex. 1-11 | None | — | — | — | 156 |
| Comp. Ex. 1-12 | None | — | — | — | 160 |
| Comp. Ex. 1-13 | None | — | — | — | 210 |
| Comp. Ex. 1-14 | None | 7.06 | 12.5 | 10000 | 170 |
| Comp. Ref. Ex. 1-1 | — | — | — | — | 180 |

In Table 1, '—' means that measurement was not carried out.

<Performance of Pest Repellent Resin Compositions>

TABLE 2

| Repellent used | Amount of repellent added (%) | Amount of repellent chemical (%) | Molding properties Foaming | Molding properties Bad smell | Molding properties Coloration | Initial percentage repellence (%) | Post-heating percentage repellence (%) | Post-water resistance percentage repellence (%) |
|---|---|---|---|---|---|---|---|---|
| Example 1-1 | 5 | 0.15 | None | None | None | 10 | 0 | — |
| As above | 10 | 0.3 | None | None | None | 60 | 53 | 48 |
| Example 1-2 | 3 | 0.15 | None | None | None | 19 | 0 | — |
| As above | 6 | 0.3 | None | None | None | 55 | 51 | 38 |
| Example 1-3 | 3 | 0.3 | None | None | None | 73 | 65 | 52 |
| Example 1-4 | 2 | 0.3 | None | None | None | 89 | 82 | 66 |
| Example 1-5 | 1 | 0.15 | None | None | None | 67 | 59 | 50 |
| As above | 1.5 | 0.3 | Some | None | Some | 91 | 78 | 62 |
| Example 1-6 | 3 | 0.3 | None | None | None | 74 | 70 | 53 |
| Example 1-7 | 3 | 0.3 | None | None | None | 68 | 66 | 52 |
| Example 1-8 | 2 | 0.3 | None | None | None | 83 | 78 | 65 |
| Example 1-9 | 1.5 | 0.3 | None | None | None | 63 | 52 | 45 |
| As above | 2 | 0.4 | Some | None | Some | 88 | 75 | 59 |
| Example 1-10 | 2 | 0.3 | None | None | None | 91 | 82 | 71 |
| Comp. Ex. 1-1 | 2 | 0.3 | Some | Some | None | 22 | 0 | — |
| Comp. Ex. 1-2 | 2 | 0.3 | Some | Some | None | 23 | 0 | — |
| Comp. Ex. 1-3 | 2 | 0.3 | Some | Some | None | 40 | 24 | 11 |
| Comp. Ex. 1-4 | 2 | 0.3 | Some | None | Some | 35 | 27 | 21 |
| Comp. Ex. 1-5 | 2 | 0.3 | None | None | Some | 51 | 45 | 35 |
| Comp. Ex. 1-6 | 2 | 0.3 | None | None | Some | 49 | 40 | 33 |
| Comp. Ex. 1-7 | 2 | 0.3 | Some | None | Some | 43 | 24 | 11 |
| Comp. Ex. 1-8 | 2 | 0.3 | Some | Some | None | 52 | 38 | 20 |
| Comp. Ex. 1-9 | 1 | 0.3 | Some | None | None | 44 | 25 | 11 |
| As above | 2 | 0.6 | Some | Some | None | 55 | 33 | 23 |
| Comp. Ex. 1-10 | 1 | 0.3 | Some | None | None | 39 | 23 | 10 |
| As above | 2 | 0.6 | Some | Some | None | 52 | 30 | 21 |
| Comp. Ex. 1-11 | 2 | 0.3 | Some | Some | Some | 44 | 29 | 12 |
| Comp. Ex. 1-12 | 1.3 | 0.3 | None | None | None | 36 | 18 | 21 |
| Comp. Ex. 1-13 | 1.5 | 0.3 | None | None | Some | 27 | 22 | 25 |

TABLE 2-continued

| Repellent used | Amount of repellent added (%) | Amount of repellent chemical (%) | Molding properties | | | Initial percentage repellence (%) | Post-heating percentage repellence (%) | Post-water resistance percentage repellence (%) |
|---|---|---|---|---|---|---|---|---|
| | | | Foaming | Bad smell | Coloration | | | |
| Comp. Ex. 1-14 | 3 | 0.3 | None | Some | None | 32 | 11 | 20 |
| Comp. Ref. Ex. 1-1 | 0.3 | 0.3 | Some | Some | None | 21 | 0 | — |
| Comp. Ref. Ex. 1-2 | 0 | 0 | None | None | None | 0 | — | — |

In Table 2, '—' means that measurement was not carried out.

Example 2-1

Durable pest repellent 2-1 was obtained by adding 0.2 g of deionized water and 0.53 g (2 mmol) of 1-piperidinecarboxylic acid-2-(2-hydroxyethyl)-1-methylpropyl ester to 10.0 g of the layered silicate A obtained in Reference Example 1 and mixing well using a mortar. When a powder X-ray diffraction was measured, it was found that there was a peak at 2θ=5.84° (d=15.1 angstroms) with an intensity of 88000 cps.

The carbon content was determined from the analytical results of the gas obtained by burning durable pest repellent 2-1 at 950° C. in oxygen/He mixed gas using a CHN elemental analyzer (model MT-5, Yanagimoto Seisakujo); when it was assumed that the carbon content was derived from 1-piperidinecarboxylic acid-2-(2-hydroxyethyl)-1-methylpropyl ester and calculation was carried out by multiplying by the molecular weight, the amount of 1-piperidinecarboxylic acid-2-(2-hydroxyethyl)-1-methylpropyl ester supported was 5 mass %, and it coincided with the amount supported calculated from the amount added.

Figure 7:
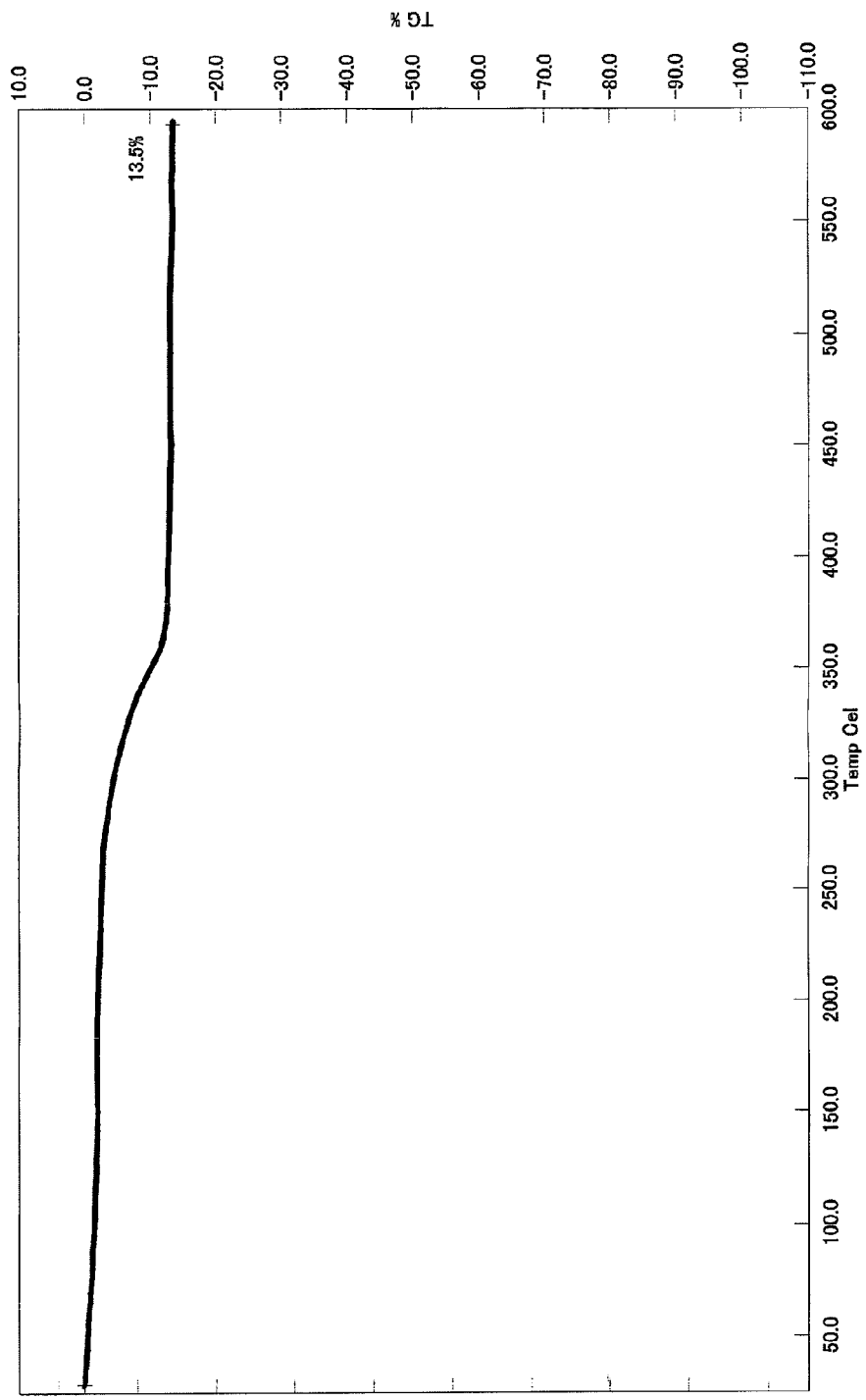
FIG. 7: A thermal analysis measurement chart showing thermogravimetric change of durable pest repellent 2-7 obtained in Example 2-7.

Furthermore, it was confirmed by thermal analysis that the supported 1-piperidinecarboxylic acid-2-(2-hydroxyethyl)-1-methylpropyl ester acquired heat resistance. The thermal analysis was carried out using a Model TG/DTA220 manufactured by Seiko Instruments under an air atmosphere, the measurement temperature was 30° C. to 600° C., and the rate of temperature increase was 20° C./min. Since the measurement is carried out in air, the overall heat resistance in air including vaporization and oxidative decomposition can be evaluated, and 1-piperidinecarboxylic acid-2-(2-hydroxyethyl)-1-methylpropyl ester that only adheres to the surface of a porous substance having a large specific surface area is subjected to oxidative decomposition at relatively low temperature and the weight decreases, whereas it is expected that 1-piperidinecarboxylic acid-2-(2-hydroxyethyl)-1-methylpropyl ester that is packed between layers of the inorganic layered compound without gaps is resistant to vaporization and oxidative decomposition and the weight will be maintained up to a higher temperature. For example, as is clear from a comparison between FIG. 7 and FIG. 8, even looking only at the temperature of the inflection point at which the supported chemical is rapidly lost makes it clear that the heat resistance of the durable pest repellent of the present invention is higher, but in order to make the comparison easier with figures, the temperature at which the amount of supported chemical component has been reduced by ⅓ is read off from the measurement results of the thermal analysis, defined as the 'heat resistance', and is shown in Table 3.

Example 2-2

Durable pest repellent 2-2 was obtained by adding 0.2 g of deionized water and 1.1 g (5 mmol) of 1-piperidinecarboxylic acid-2-(2-hydroxyethyl)-1-methylpropyl ester to 10.0 g of layered silicate A obtained in Reference Example 1 and mixing well using a mortar. When a powder X-ray diffraction was measured, it was found that there was a peak at 2θ=5.82° (d=15.2 angstroms) with an intensity of 120000 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 10 mass %, and it coincided with the amount supported calculated from the amount added. Furthermore, a figure for the heat resistance was obtained by carrying out a thermal analysis and is shown in Table 3.

Example 2-3

Durable pest repellent 2-3 was obtained by adding 0.2 g of deionized water and 1.7 g (8 mmol) of 1-piperidinecarboxylic acid-2-(2-hydroxyethyl)-1-methylpropyl ester to 10.0 g of layered silicate A obtained in Reference Example 1 and mixing well using a mortar. When a powder X-ray diffraction was measured, it was found that there was a peak at 2θ=5.26° (d=16.8 angstroms) with an intensity of 120000 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 15 mass %, and it coincided with the amount supported calculated from the amount added. Furthermore, a figure for the heat resistance was obtained by carrying out a thermal analysis and is shown in Table 3.

Example 2-4

Pest repellent 2-4 was obtained by adding 0.2 g of deionized water and 2.5 g (10 mmol) of 1-piperidinecarboxylic acid-2-(2-hydroxyethyl)-1-methylpropyl ester to 10.0 g of layered silicate A obtained in Reference Example 1 and mixing well using a mortar. When a powder X-ray diffraction was measured, it was found that there was a peak at 2θ=5.26° (d=16.8 angstroms) with an intensity of 92000 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 20 mass %, and it coincided with the amount supported calculated from the amount added. Furthermore, a figure for the heat resistance was obtained by carrying out a thermal analysis and is shown in Table 3.

Example 2-5

Pest repellent 2-5 was obtained by adding 0.2 g of deionized water and 3.3 g (14 mmol) of 1-piperidinecarboxylic acid-2-(2-hydroxyethyl)-1-methylpropyl ester to 10.0 g of layered silicate A obtained in Reference Example 1 and mixing well using a mortar. When a powder X-ray diffraction was measured, it was found that there was a peak at 2θ=5.18° (d=17.0 angstroms) with an intensity of 80000 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 25 mass %, and it coincided with the amount supported calculated from the amount added. Furthermore, a figure for the heat resistance was obtained by carrying out a thermal analysis and is shown in Table 3.

Example 2-6

Pest repellent 2-6 was obtained by adding 0.2 g of pure water and 0.53 g (2 mmol) of 1-piperidinecarboxylic acid-2-(2-hydroxyethyl)-1-methylpropyl ester to 10.0 g of layered silicate B obtained in Reference Example 2 and mixing well using a mortar. When a powder X-ray diffraction was measured, it was found that there was a peak at 2θ=5.98° (d=14.8 angstroms) with an intensity of 31000 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 5 mass %, and it coincided with the amount supported calculated from the amount added. Furthermore, a figure for the heat resistance was obtained by carrying out a thermal analysis and is shown in Table 3.

Example 2-7

Pest repellent 2-7 was obtained by adding 0.2 g of deionized water and 1.1 g (5 mmol) of 1-piperidinecarboxylic acid-2-(2-hydroxyethyl)-1-methylpropyl ester to 10.0 g of layered silicate B obtained in Reference Example 2 and mixing well using a mortar. When a powder X-ray diffraction was measured, it was found that there was a peak at 2θ=5.98° (d=14.8 angstroms) with an intensity of 70000 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 10 mass %, and it coincided with the amount supported calculated from the amount added. Furthermore, a figure for the heat resistance was obtained by carrying out a thermal analysis and is shown in Table 3.

Example 2-8

Pest repellent 2-8 was obtained by adding 0.2 g of deionized water and 1.7 g (8 mmol) of 1-piperidinecarboxylic acid-2-(2-hydroxyethyl)-1-methylpropyl ester to 10.0 g of layered silicate B obtained in Reference Example 2 and mixing well using a mortar. When a powder X-ray diffraction was measured, it was found that there was a peak at 2θ=5.98° (d=14.8 angstroms) with an intensity of 75000 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 15 mass %, and it coincided with the amount supported calculated from the amount added. Furthermore, a figure for the heat resistance was obtained by carrying out a thermal analysis and is shown in Table 3.

Example 2-9

Pest repellent 2-9 was obtained by adding 0.2 g of deionized water and 2.5 g (10 mmol) of 1-piperidinecarboxylic acid-2-(2-hydroxyethyl)-1-methylpropyl ester to 10.0 g of layered silicate B obtained in Reference Example 2 and mixing well using a mortar. When a powder X-ray diffraction was measured, it was found that there was a peak at 2θ=4.78° (d=18.5 angstroms) with an intensity of 70000 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 20 mass %, and it coincided with the amount supported calculated from the amount added. Furthermore, a figure for the heat resistance was obtained by carrying out a thermal analysis and is shown in Table 3.

Example 2-10

Pest repellent 2-10 was obtained by adding 0.2 g of deionized water and 3.3 g (14 mmol) of 1-piperidinecarboxylic acid-2-(2-hydroxyethyl)-1-methylpropyl ester to 10.0 g of layered silicate C obtained in Reference Example 3 and mixing well using a mortar. When a powder X-ray diffraction was measured, it was found that there was a peak at 2θ=4.66° (d=18.9 angstroms) with an intensity of 150000 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 25 mass %, and it coincided with the amount supported calculated from the amount added. Furthermore, a figure for the heat resistance was obtained by carrying out a thermal analysis and is shown in Table 3.

Example 2-11

Pest repellent 2-11 was obtained by adding 0.2 g of pure water and 1.1 g (5 mmol) of 1-piperidinecarboxylic acid-2-(2-hydroxyethyl)-1-methylpropyl ester to 10.0 g of layered silicate C obtained in Reference Example 3 and mixing well using a mortar. When a powder X-ray diffraction was measured, it was found that there was a peak at 2θ=5.84° (d=15.1 angstroms) with an intensity of 4200 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 10 mass %, and it coincided with the amount supported calculated from the amount added. Furthermore, a figure for the heat resistance was obtained by carrying out a thermal analysis and is shown in Table 3.

Example 2-12

Pest repellent 2-12 was obtained by adding 0.2 g of pure water and 1.7 g (8 mmol) of 1-piperidinecarboxylic acid-2-(2-hydroxyethyl)-1-methylpropyl ester to 10.0 g of layered silicate C obtained in Reference Example 3 and mixing well using a mortar. When a powder X-ray diffraction was measured, it was found that there was a peak at 2θ=5.56° (d=15.9 angstroms) with an intensity of 5200 cps. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 15 mass %, and it coincided with the amount supported calculated from the amount added. Furthermore, a figure for the heat resistance was obtained by carrying out a thermal analysis and is shown in Table 3.

Comparative Example 2-1

Figure 8:
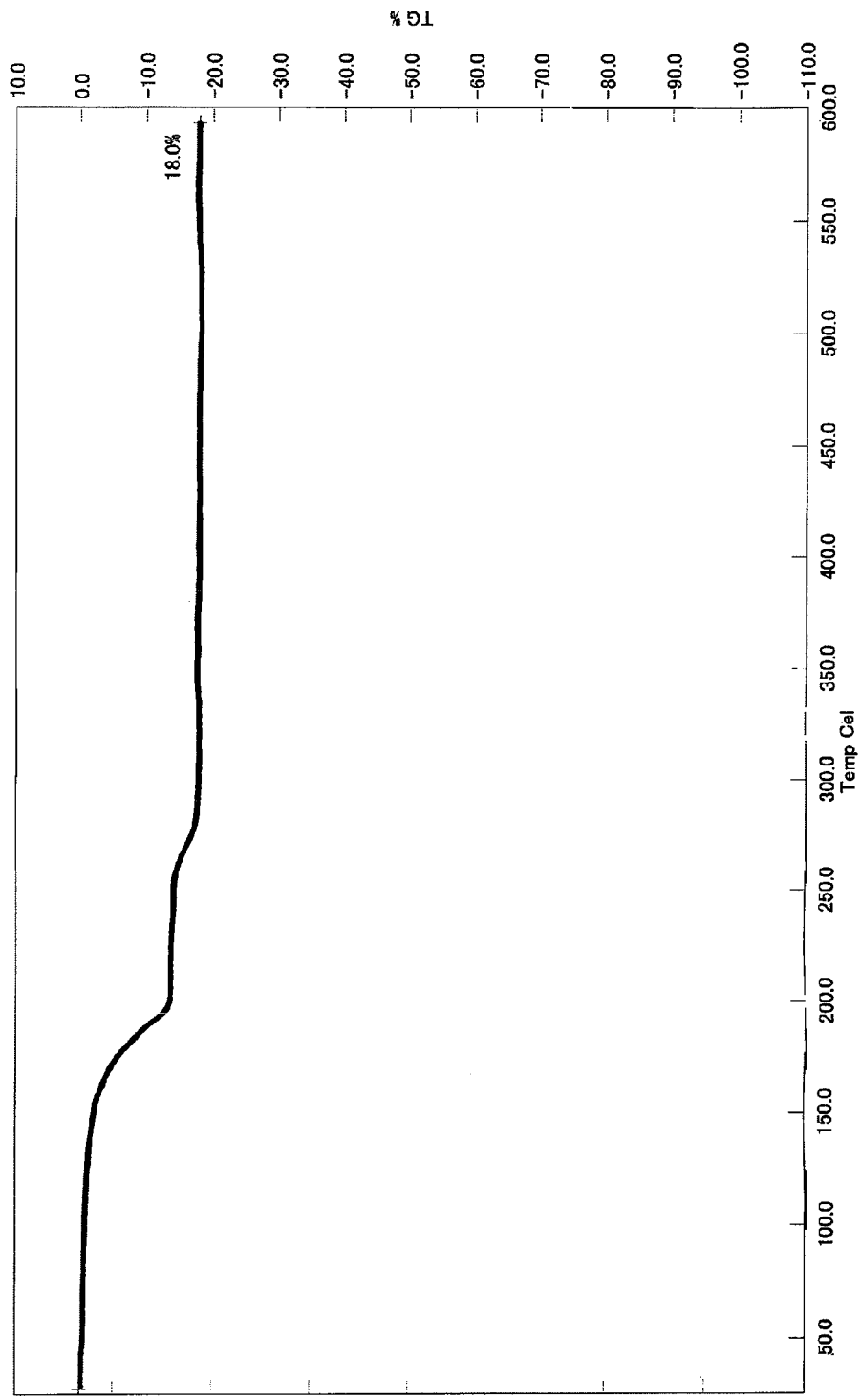
FIG. 8: A thermal analysis measurement chart showing thermogravimetric change of comparative pest repellent 2-1 obtained in Comparative Example 2-1.

Comparative pest repellent 2-1 was obtained by adding 1.7 g (8 mmol) of 1-piperidinecarboxylic acid-2-(2-hydroxyethyl)-1-methylpropyl ester to 10.0 g of layered silicate A obtained in Reference Example 1 and mixing well using a mortar. When a powder X-ray diffraction was measured, it was found that there was a peak at 2θ=7.06° (d=12.5 angstroms) with an intensity of 12000 cps. The value for d is the same as the result of powder X ray measurement for layered silicate A before adding 1-piperidinecarboxylic acid-2-(2-hydroxyethyl)-1-methylpropyl ester, suggesting that the added 1-piperidinecarboxylic acid-2-(2-hydroxyethyl)-1-methylpropyl ester did not enter between the layers of layered silicate A at all. However, when the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 15 mass %, and it coincided with the amount supported calculated from the amount added. This suggests that 1-piperidinecarboxylic acid-2-(2-hydroxyethyl)-1-methylpropyl ester adheres to on the surface of layered silicate A. Furthermore, a figure for the heat resistance was obtained by carrying out a thermal analysis and is shown in Table 3. A chart of the thermal analysis is shown in FIG. 8; there is a clear difference compared with the thermal analysis chart (FIG. 7) of Example 2-7, and there is also a difference in value for the heat resistance in Table 3.

Comparative Example 2-2

Comparative pest repellent 2-2 was obtained by adding 0.5 g of hexane and 1.7 g (8 mmol) of 1-piperidinecarboxylic acid-2-(2-hydroxyethyl)-1-methylpropyl ester to 10.0 g of the layered silicate A obtained in Reference Example 1, mixing well using a mortar, and drying at 90° C. for 2 hours. When a powder X-ray diffraction was measured, it was found that there was a peak at 2θ=7.06° (d=12.5 angstroms) with an intensity of 10000 cps. The value for d is the same as the result of powder X ray measurement for layered silicate A before adding 1-piperidinecarboxylic acid-2-(2-hydroxyethyl)-1-methylpropyl ester, suggesting that the added 1-piperidinecarboxylic acid-2-(2-hydroxyethyl)-1-methylpropyl ester did not enter between the layers of layered silicate A at all. However, when the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 15 mass %, and it coincided with the amount supported calculated from the amount added. This suggests that 1-piperidinecarboxylic acid-2-(2-hydroxyethyl)-1-methylpropyl ester adheres to on the surface of layered silicate A. Furthermore, a figure for the heat resistance was obtained by carrying out a thermal analysis and is shown in Table 3.

Comparative Example 2-3

Comparative pest repellent composition 3 was obtained by adding 0.2 g of pure water and 1.7 g (8 mmol) of 1-piperidinecarboxylic acid-2-(2-hydroxyethyl)-1-methylpropyl ester to 10.0 g of silica gel and mixing well using a mortar. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 15 mass %, and it coincided with the amount supported calculated from the amount added. Furthermore, a figure for the heat resistance was obtained by carrying out a thermal analysis and is shown in Table 3.

Comparative Example 2-4

Comparative pest repellent composition 4 was obtained by adding 0.2 g of pure water and 1.7 g (8 mmol) of 1-piperidinecarboxylic acid-2-(2-hydroxyethyl)-1-methylpropyl ester to 10.0 g of aluminum silicate (Kyowaad 700 manufactured by Kyowa Chemical Industry Co., Ltd.) and mixing well using a mortar. When the carbon content was measured in the same manner as in Example 2-1 using a CHN elemental analyzer and the amount of 1-piperidinecarboxylic acid-2-(2-hydroxyethyl)-1-methylpropyl ester supported was calculated, it was found to be 15 mass %, and it coincided with the amount supported calculated from the amount added. Furthermore, a figure for the heat resistance was obtained by carrying out a thermal analysis and is shown in Table 3.

Comparative Reference Example 2-1

In Comparative Reference Example 2-1, 1-piperidinecarboxylic acid-2-(2-hydroxyethyl)-1-methylpropyl ester was used as the pest repellent chemical. An inorganic substance was not used in combination, and powder X-ray diffraction measurement was therefore not carried out. Furthermore, a figure for the heat resistance was obtained by carrying out a thermal analysis, and the result is shown in Table 3.

<Evaluation of Resin Moldability>

The durable pest repellents prepared in Examples 2-1 to 2-12, the comparative pest repellents prepared in Comparative Examples 2-1 to 2-4, and Comparative Reference Example 2-1 were mixed with a polyethylene resin (PE-NUC-8350, Nippon Unicar Co., Ltd.). For example, in the durable pest repellent of Example 2-1, since the amount of pest repellent chemical supported was 5 mass %, when the amount of repellent added in a resin composition shown in Table 4 was 3%, the amount of pest repellent chemical added was calculated as 0.15 mass %, and when the amount of repellent added in the resin composition was 10%, the amount of pest repellent chemical added was calculated as 0.3 mass %.

Resin compositions were produced by adjusting the amount of each repellent added to the resin composition so that the amount of pest repellent chemical added in the resin composition was 0.1 to 0.9%, they were injection-molded into flat plates, and evaluation of whether kneading into the resin was possible was carried out. Molding was carried out using a Model M-50A(II)-DM manufactured by Meiki Co., Ltd. at a molding temperature of 250° C., thus giving 10 cm square plates having a thickness of 2 mm. Furthermore, the residence time was 5 minutes, and checks as to whether or not there was foaming, a strange smell, or discoloration during molding were carried out. The results are shown in Table 4. A plate was molded without adding any chemical and defined as Comparative Reference Example 2-2.

<Evaluation of Repellency>

Plates molded after adding the durable pest repellents prepared in Examples 2-1 to 2-4, comparative pest repellents prepared in Comparative Examples 2-1 to 2-4, and Comparative Reference Example 2-1 to a polyethylene resin (PE- NUC-8350 manufactured by Nippon Unicar Co., Ltd.) so that the pest repellent chemical was 0.3 mass % of the entire resin composition were cut into circles having a diameter of a little under 4 cm and subjected to a test for anti-mite properties. The test was carried by an intrusion-prevention method in accordance with JIS L 1920 'Testing methods for efficacy against house dust mite of textiles'. The results (percentage repellency) of the test for anti-mite properties are shown in Table 4.

<Evaluation of Persistence of Repellence>

Plates molded after adding the durable pest repellents prepared in Examples 2-1 to 2-12, the comparative pest repellents prepared in Comparative Examples 2-1 to 2-4, and Comparative Reference Example 2-1 to a polyethylene resin (PE-NUC-8350 manufactured by Nippon Unicar Co., Ltd.) so that the pest repellent component was 0.3 mass % were held in a dryer at 81° C. for 48 hours. They were cut into circles having a diameter of a little under 4 cm and subjected to a test for anti-mite properties. The test was carried by an intrusion-prevention method in accordance with JIS L 1920 'Testing methods for efficacy against house dust mite of textiles'. The results (percentage repellency) of the test for anti-mite properties are shown in Table 4.

<Evaluation of Water Resistant Persistence of Repellence>

Flat plates were injection-molded using pest repellent resin compositions obtained by adding the durable pest repellents prepared in Examples 2-1 to 2-12, comparative pest repellents prepared in and Comparative Examples 2-1 to 2-4, and Comparative Reference Example 2-1 to a polyethylene resin (PE-NUC-8350, Nippon Unicar Co., Ltd.) at 0.3 mass %. The flat plate was immersed in hot water at 50° C. for 16 hours to thus carry out a water resistant persistence test. The flat plate after the test was cut into a disc having a diameter of a little under 4 cm and subjected to a test for anti-mite properties. The test was carried by an intrusion-prevention method in accordance with JIS L 1920 'Testing methods for efficacy against house dust mite of textiles'. The results (percentage repellency) of the test for anti-mite properties are shown in Table 4.

<Properties of Pest Repellents>

TABLE 3

| | Solvent and amount added | Peak due to (002) plane 2θ (°) | Plane distance of (002) plane d (Å) | Peak intensity of (002) plane (cps) | Heat resistance (° C.) |
|---|---|---|---|---|---|
| Example 2-1 | Water 2% | 5.84 | 15.1 | 88000 | 266 |
| Example 2-2 | Water 2% | 5.82 | 15.2 | 120000 | 251 |
| Example 2-3 | Water 2% | 5.26 | 16.8 | 120000 | 240 |
| Example 2-4 | Water 2% | 5.26 | 16.8 | 92000 | 223 |
| Example 2-5 | Water 2% | 5.18 | 17 | 80000 | 195 |
| Example 2-6 | Water 2% | 5.98 | 14.8 | 31000 | 296 |
| Example 2-7 | Water 2% | 5.98 | 14.8 | 70000 | 288 |
| Example 2-8 | Water 2% | 5.98 | 14.8 | 75000 | 278 |
| Example 2-9 | Water 2% | 4.78 | 18.5 | 70000 | 250 |
| Example 2-10 | Water 2% | 4.66 | 18.9 | 150000 | 185 |
| Example 2-11 | Water 2% | 5.84 | 15.1 | 4200 | 266 |
| Example 2-12 | Water 2% | 5.56 | 15.9 | 5200 | 198 |
| Comp. Ex. 2-1 | None | 7.06 | 12.5 | 12000 | 188 |
| Comp. Ex. 2-2 | Hexane 5% | 7.06 | 12.5 | 10000 | 184 |
| Comp. Ex. 2-3 | Water 2% | — | — | — | 168 |
| Comp. Ex. 2-4 | Water 2% | — | — | — | 170 |
| Comp. Ref. Ex. 2-1 | — | — | — | — | 185 |

In Table 3, '—' means that measurement was not carried out.

<Performance of Pest Repellent Resin Compositions>

TABLE 4

| Repellent used | Amount of repellent added (%) | Amount of repellent chemical (%) | Molding properties | | | Initial percentage repellence (%) | Post-heating percentage repellence (%) | Post-water resistance percentage repellence (%) |
|---|---|---|---|---|---|---|---|---|
| | | | Foaming | Bad smell | Coloration | | | |
| Example 2-1 | 3 | 0.15 | None | None | None | 20 | 0 | — |
| As above | 6 | 0.3 | None | None | None | 45 | 42 | 20 |
| Example 2-2 | 2 | 0.2 | None | None | None | 25 | 0 | — |
| As above | 3 | 0.3 | None | None | None | 52 | 48 | 33 |
| Example 2-3 | 2 | 0.3 | None | None | None | 78 | 71 | 53 |
| Example 2-4 | 1.5 | 0.3 | None | None | None | 80 | 71 | 49 |
| As above | 2 | 0.4 | None | None | None | 85 | 75 | 53 |
| Example 2-5 | 1.2 | 0.3 | None | None | None | 81 | 73 | 55 |
| As above | 2 | 0.5 | Some | None | None | 88 | 77 | 59 |
| Example 2-6 | 3 | 0.1 | None | None | None | 15 | 0 | — |
| As above | 6 | 0.2 | None | None | None | 40 | 36 | 23 |
| Example 2-7 | 2 | 0.2 | None | None | None | 22 | 0 | — |
| As above | 3 | 0.3 | None | None | None | 58 | 57 | 39 |
| Example 2-8 | 2 | 0.3 | None | None | None | 63 | 59 | 51 |
| Example 2-9 | 1.5 | 0.3 | None | None | None | 67 | 66 | 53 |
| As above | 2 | 0.4 | None | None | Some | 75 | 70 | 58 |

TABLE 4-continued

| Repellent used | Amount of repellent added (%) | Amount of repellent chemical (%) | Molding properties | | | Initial percentage repellence (%) | Post-heating percentage repellence (%) | Post-water resistance percentage repellence (%) |
| --- | --- | --- | --- | --- | --- | --- | --- | --- |
| | | | Foaming | Bad smell | Coloration | | | |
| Example 2-10 | 1.2 | 0.3 | None | None | None | 71 | 63 | 55 |
| As above | 2 | 0.5 | Some | None | Some | 80 | 69 | 66 |
| Example 2-11 | 3 | 0.3 | None | None | None | 88 | 75 | 59 |
| Example 2-12 | 6 | 0.9 | None | None | None | 91 | 82 | 71 |
| Comp. Ex. 2-1 | 2 | 0.3 | Some | Some | None | 22 | 0 | — |
| Comp. Ex. 2-2 | 2 | 0.3 | Some | Some | None | 26 | 0 | — |
| Comp. Ex. 2-3 | 2 | 0.3 | Some | None | None | 24 | 0 | — |
| Comp. Ex. 2-4 | 2 | 0.3 | Some | Some | None | 19 | 0 | — |
| Comp. Ref. Ex. 2-1 | 0.3 | 0.3 | Some | Some | None | 22 | 0 | — |
| Comp. Ref. Ex. 2-2 | 0 | 0 | None | None | None | 0 | — | — |

In Table 4, '—' means that measurement was not carried out.

It can be seen from Tables 1 to 4 that the durable pest repellent of the present invention has excellent heat resistance and can be kneaded into a resin, and the resin composition has excellent pest repellent performance, the pest repellent effect having excellent persistence.

Example 3-1

A plate molded using, as durable pest repellent 3-1, an equal weight mixture of durable pest repellent 1-2 obtained in Example 1-2 and durable pest repellent 2-1 obtained in Example 2-1 in the same manner as in Example 1-2 so that the total of pest repellent chemicals was 0.3 mass % of the entire resin composition was subjected to a test for anti-mite properties, evaluation of persistence of repellence, and evaluation of water resistant persistence of repellence, and the results are shown in Table 5.

Example 3-2

Durable pest repellent 3-2 was obtained by adding a mixture of 0.27 g (1.5 mmol) of N,N-diethyl-m-toluamide and 0.27 g (1 mmol) of 1-piperidinecarboxylic acid-2-(2-hydroxyethyl)-1-methylpropyl ester to 0.2 g of deionized water, then adding 10.0 g of the layered silicate A obtained in Reference Example 1 thereto, and mixing well using a mortar. This was subjected to a test for anti-mite properties, evaluation of persistence of repellence, and evaluation of water resistant persistence of repellence in the same manner as for durable pest repellent 3-1, and the results are shown in Table 5.

<Performance of Pest Repellent Resin Compositions> acid-2-(2-hydroxyethyl)-1-methylpropyl ester, the performance of the resin composition after the water resistance test or the heat resistance test was better than a case in which separate durable pest repellents were used in combination.

Furthermore, it can be seen that, with regard to those employing a different supporting method from that in the present invention or using a different support, either the heat resistance during molding or the persistence of the pest repellent performance was poor, and use by kneading into a resin was impossible.

INDUSTRIAL APPLICABILITY

Since the durable pest repellent of the present invention has excellent heat resistance and persistence, it can be kneaded into a resin. It can be used by kneading into a synthetic fiber or can be used in clothing, nets, screens, carpets, curtains, hanging wardrobes, tents, sheets, electrical appliances, agricultural tools, etc.

EXPLANATION OF REFERENCE NUMERALS AND SYMBOLS

The abscissa of FIG. 1, FIG. 2, FIG. 5, and FIG. 6 denotes X-ray diffraction angle 2θ (units °), and the ordinate denotes diffraction intensity (units cps).

The abscissa of FIG. 3, FIG. 4, FIG. 7, and FIG. 8 denotes temperature (units ° C.), the ordinate denotes thermogravimetric change (units %), corresponding to percentage thermogravimetric loss relative to the weight of the pest repellent at the temperature (30° C.) at which temperature increase was started.

TABLE 5

| Repellent used | Amount of repellent added (%) | Amount of repellent chemical (%) | Molding properties | | | Initial percentage repellence (%) | Post-heating percentage repellence (%) | Post-water resistance percentage repellence (%) |
| --- | --- | --- | --- | --- | --- | --- | --- | --- |
| | | | Foaming | Bad smell | Coloration | | | |
| Example 3-1 | 6 | 0.3 | None | None | None | 50 | 46 | 29 |
| Example 3-2 | 6 | 0.3 | None | None | None | 50 | 48 | 31 |

The results of Table 5 show that when a durable pest repellent was produced using as a pest repellent chemical a mixture of N,N-diethyl-m-toluamide and 1-piperidinecarboxylic

What is claimed is:

1. A durable pest repellent in which a pest repellent chemical containing as an essential component at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester is supported within layers of a layered silicate represented by Formula [2] or Formula [3] below:

  [2]

  [3]

wherein ($M^1$) is Ca and/or Zn, (A) means F and/or OH, $2a+2b+c=6$, $0.001<c\leq0.55$, and $0.2<a<3$.

2. The durable pest repellent according to claim 1, wherein the layered silicate has a powder X-ray diffraction pattern in which an (002) plane peak indicating interlayer spacing is in a range of $2\theta=5.0°$ to $6.3°$.

3. The durable pest repellent according to claim 1, wherein in Formula [2] b satisfies $2.3<b<2.8$, and c satisfies $0.001<c<0.3$.

4. The durable pest repellent according to claim 1, wherein, in Formula [3] b satisfies $2.5<b<3$, and c satisfies $0.15<c<0.5$.

5. The durable pest repellent according to claim 1, wherein the total amount supported of N,N-diethyl-m-toluamide and 1-piperidinecarboxylic acid-2-(2-hydroxyethyl)-1-methylpropyl ester is 0.3 to 1.2 mmol relative to 1 g of the layered silicate.

6. The durable pest repellent according to claim 1, wherein the layered silicate has an average particle size of no greater than 10 μm.

7. A process for producing the durable pest repellent according to claim 1, the process comprising adding 0.5 to 5 mass % of deionized water to the layered silicate and mixing at least one selected from N,N-diethyl-m-toluamide, 1-piperidinecarboxylic acid-2-(2-hydroxyethyl)-1-methylpropyl ester, and N,N-diethyl-m-toluamide and 1-piperidinecarboxylic acid-2-(2-hydroxyethyl)-1-methylpropyl ester.

8. A pest repellent resin composition comprising the durable pest repellent according to claim 1.

* * * * *